United States Patent [19]
Katakura

[11] Patent Number: 5,341,809
[45] Date of Patent: Aug. 30, 1994

[54] ULTRASONIC FLOWMETER

[75] Inventor: Kageyoshi Katakura, Tokyo, Japan

[73] Assignee: Hitachi, Ltd., Tokyo, Japan

[21] Appl. No.: 845,949

[22] Filed: Mar. 4, 1992

Related U.S. Application Data

[63] Continuation-in-part of Ser. No. 575,572, Aug. 31, 1990, abandoned.

[30] Foreign Application Priority Data

Mar. 4, 1991 [JP] Japan ................... 3-062719

[51] Int. Cl.$^5$ ................................ A61B 8/06
[52] U.S. Cl. ................ 128/661.09; 73/861.25
[58] Field of Search ............ 128/661.08–661.10; 73/861.25

[56] References Cited

U.S. PATENT DOCUMENTS

| | | | |
|---|---|---|---|
| 4,265,126 | 5/1981 | Papadofrangokis et al. | 128/661.09 X |
| 4,759,375 | 7/1988 | Namekawa et al. | 128/661.09 |
| 4,905,206 | 2/1990 | Nishiyama et al. | 128/661.09 X |
| 4,930,513 | 6/1990 | Mayo et al. | 128/661.09 |
| 4,979,513 | 12/1990 | Sakai et al. | 128/661.09 |
| 5,201,313 | 4/1993 | Katakura | 128/661.09 |

OTHER PUBLICATIONS

IEEE Transactions on Sonics and Ultrasonics, vol. SU-32, No. 3, May 1985, pp. 458–464.

Primary Examiner—Francis Jaworski
Attorney, Agent, or Firm—Antonelli, Terry, Stout & Kraus

[57] ABSTRACT

A flowmeter employing an array of ultrasonic wave transducer elements, the flowmeter being arranged in such a way that reception signals of plural reception beams aligned in parallel with one another are formed from detection signals of reflection ultrasonic waves from the transducer elements; the Fourier transformation is performed with respect to a direction of alignment of the reception beams; a moving target indication processing is then performed among a plurality of reception signals derived from the repetitive transmissions; the result of the Fourier transformation is treated as two-dimensional signals of time series corresponding to the transmission of the ultrasonic wave, and with respect to a plurality of straight lines coinciding at respective angles with the origin of a coordinate, signal values on each of the straight lines are treated as a one-dimension sequence of numbers to perform the Fourier transformation; and an axial velocity component and a lateral (transverse) velocity component of a moving object are obtained on the basis of the resulting signal distribution.

36 Claims, 20 Drawing Sheets

F I G. 15
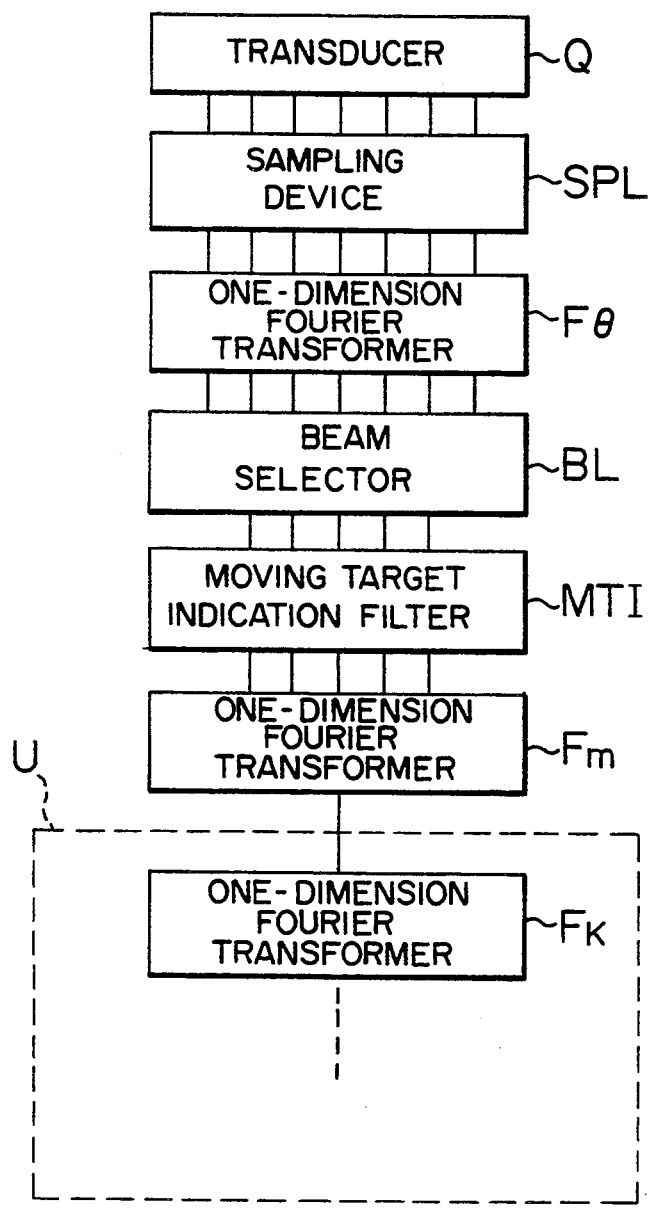

F I G. 22
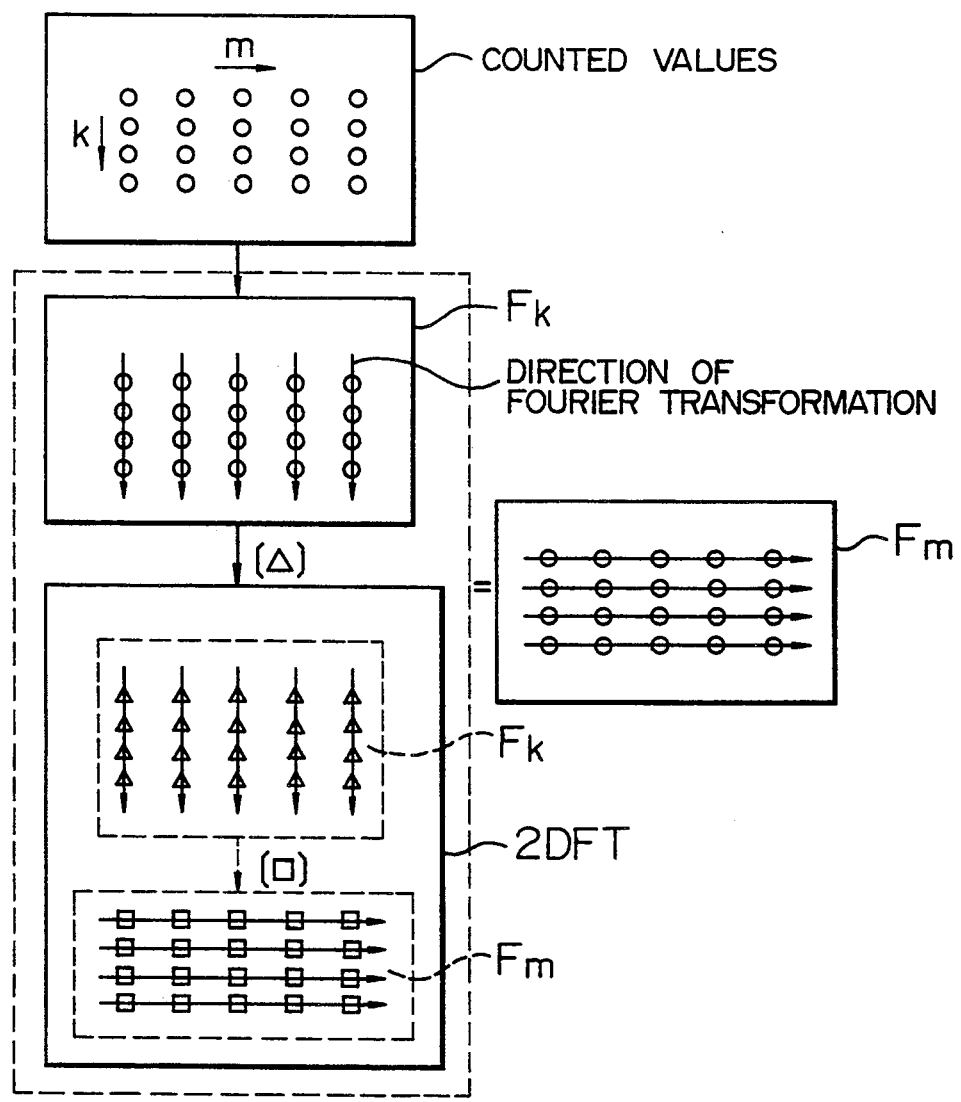

F I G. 24
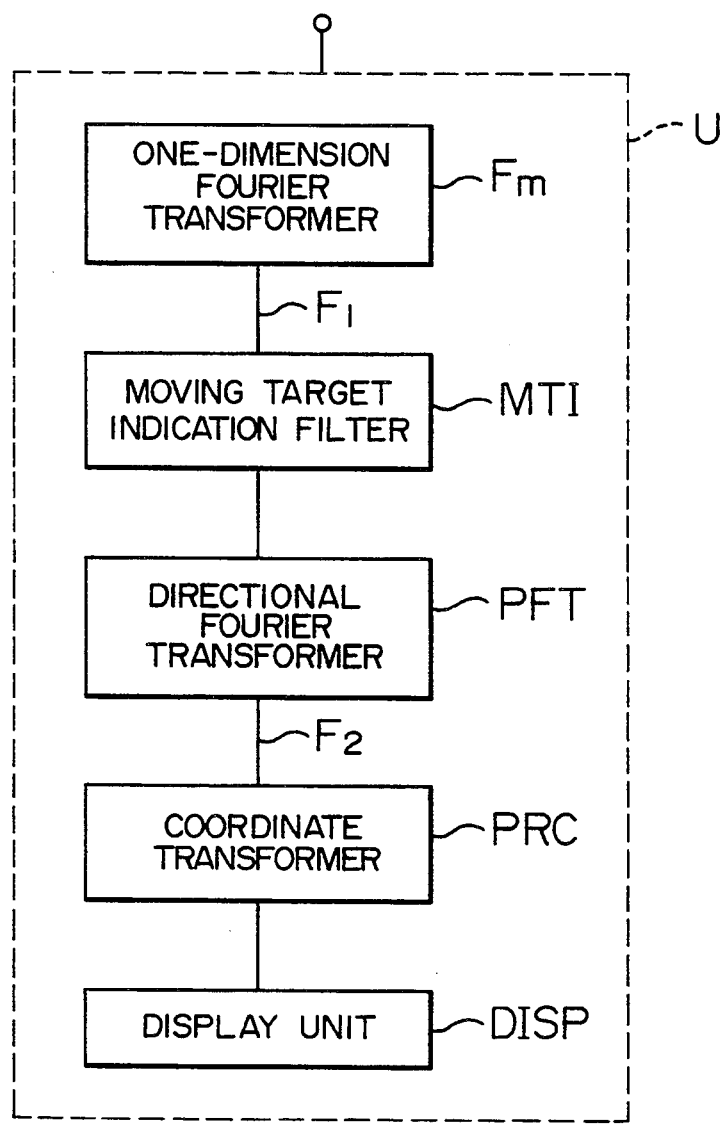

ULTRASONIC FLOWMETER

CROSS-REFERENCE TO RELATED APPLICATIONS

The present invention is a continuation-in-part application of U.S. patent application Ser. No. 07/575,572 filed on August 31, 1990, and now abandoned.

BACKGROUND OF THE INVENTION

The present invention relates to a pulsed ultrasonic flowmeter, i.e., a Doppler flowmeter, used in the fields of clinical medicine, underwater measurement, and the like, and more particularly to a flowmeter which is effective for the measurement of the blood flow in the heart.

Generally, the method of measuring the velocity of an object based on the Doppler shift of the reflected sound wave detects the component of velocity in the sound wave beam direction. In contrast, the method described in publication: Japanese Journal of Medical Ultrasonics, 40-A-56 (May 1982), pp. 395–396, calculates vectorial components of velocity from measured values based on a plurality of probes by utilization of the intersecting angle of beam.

However, the above-mentioned conventional technique bases the calculation on the measured velocities, providing only a mean value of velocity in the case of measurement of velocity in distribution, and it is not possible to calculate the spatial distribution of the flow direction.

A method of measuring the velocity at right angle with the ultrasonic beam was unveiled in an article entitled "Transverse Doppler Summary" by V. L. Newhouse. This method detects a reflected wave from the measurement position with a transducer having a wide aperture which covers the measurement position in a relatively wide angle, and evaluates the flow rate in the transverse direction from the frequency spectrum of the detected signal. However, this method can not distinguish the heading of flow in the transverse direction, i.e., the polarity of velocity. Moreover, expansion of spectrum can be caused also by existence of particles staying from main flow, and the accuracy of flow rate is not sufficient for the medical use.

SUMMARY OF THE INVENTION

Accordingly, an object of the present invention is to provide an ultrasonic flowmeter of simple construction which is capable of measuring the distribution of the flow rate.

Another object of the present invention is to provide an ultrasonic flowmeter which reveals the accurate magnitude and direction of flow, i.e., the heading of flow.

The present invention is designed in such a way as to process the signals from an array of transducer elements, thereby revealing the velocity distribution in all directions.

More specifically, the present invention resides characteristically in an ultrasonic flowmeter which comprises an ultrasonic transducer including an array of elements, means for driving repeatedly part of the transducer elements at a prescribed interval thereby to transmit an ultrasonic wave to a target, a parallel reception beam forming device which modifies the phases of the signals from the transducer elements to produce inparallel reception signals derived from reception beams with different directivities, a sampling device which samples the parallel reception signals and stores the resulting signals, means for performing moving target indication through the differential processing among signals from the sampling device having a prescribed duration since transmission, a first one-dimension Fourier transform device which performs the Fourier transformation with respect to a direction of alignment of reception beams for the output of the moving target indication means, and second Fourier transform means for performing the Fourier transformation with respect to a repetitive transmission direction for the successive outputs of the first Fourier transform device, and operates to evaluate the lateral velocity and axial velocity of a moving object in the target on the basis of the two-dimensional distribution of the outputs of the second Fourier transform means.

Further, the present invention resides characteristically in an ultrasonic flowmeter which comprises an ultrasonic transducer including an array of transducer elements, means of driving repeatedly part of the transducer elements of the ultrasonic transducer at a prescribed interval thereby to transmit an ultrasonic wave to a target, a parallel reception beam forming device which modifies the phases of the signals from the transducer elements of the ultrasonic transducer to produce in parallel reception signals drived from reception beams with different directivities, a sampling device which samples the parallel reception signals and stores therein the resulting signals, moving target indication filter means for performing moving target indication through the differential processing among signals from the sampling device having a prescribed duration since transmission, a first one-dimension Fourier transform device which performs the Fourier transformation with respect to a direction of alignment of reception beams, a second one-dimension Fourier transform device which performs the Fourier transformation in such a way as to treat outputs from the first one-dimension Fourier transform device as two-dimensional signals of time series corresponding to transmission of the ultrasonic wave and to treat, with respect to a plurality of straight lines coinciding at respective angles with the origin of a coordinate, values of signals on each of the straight lines as a one-dimension sequence of numbers thereby to perform the Fourier transformation, a coordinate transform device which transforms outputs from the second one-dimension Fourier transform device into a lateral velocity and an axial velocity of a moving object, whereby the lateral velocity and axial velocity of the moving object in the target are evaluated.

Other features of the present invention will become apparent from the following detailed description.

BRIEF DESCRIPTION OF THE DRAWINGS

FIGS. 14 through 18 and FIGS. 20 through 26 are block diagrams showing the embodiments of the present invention.

DESCRIPTION OF THE PREFERRED EMBODIMENTS

Figure 1:
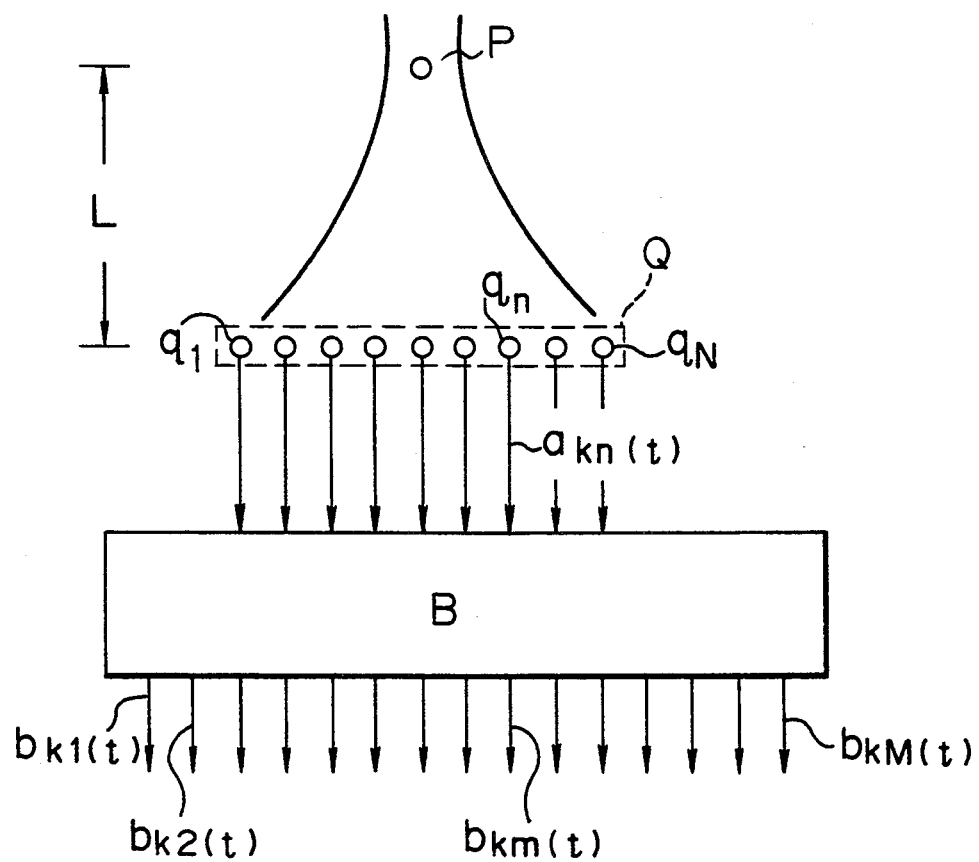
FIGS. 1 through 13 are diagrams used to explain the operation of the present invention.

FIG. 1 is a block diagram showing the arrangement of transducer elements of the present invention, where the reference symbol P designates a moving object, the reference symbol Q designates an array of transducer elements, the reference symbols $q_1$ through $q_N$ designate the transducer elements, and the reference symbol B designates a parallel beam forming device for a plurality of reception beams.

Among the array of transducer elements Q in FIG. 1, all or part of the elements transmit ultrasonic waves which focus on the point P at a time interval of $t_k$ (k=0, 1, ..., k). The distance from the array Q to the focal point P is L. The ultrasonic waves are reflected on the point P, and are received by the elements $q_n$ (n=1, 2, ..., N) of array Q which produces signals $a_{kn}(t)$.

Figure 2:
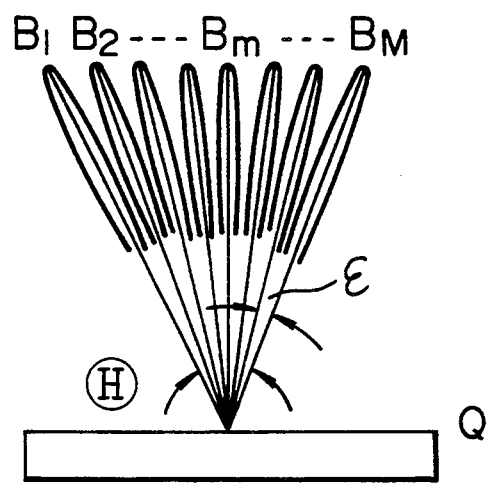

The signals $a_{kn}(t)$ are applied to a parallel beam forming section B. FIG. 2 is a view showing a beam pattern of individual reception signals of the reception beam parallel forming device B shown in FIG. 1.

Figure 3A:
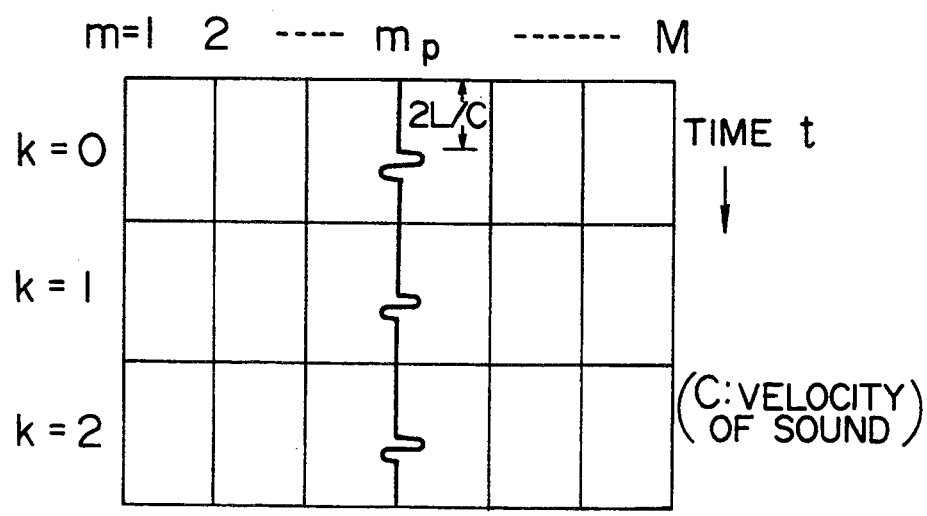
Figure 3B:
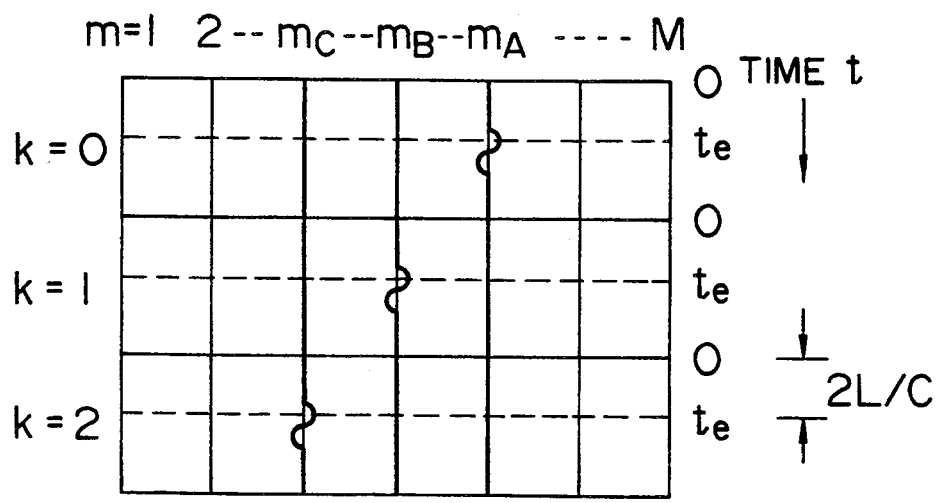

The section B produces simultaneously reception signals $b_{km}(t)$ (where m=1 to M) on the basis of the reception signals $a_{kn}(t)$ for the respective reception ultrasonic beams indicated by $B_1, B_2, ..., B_m, ..., B_M$ in FIG. 2 having a beam spacing of $\epsilon$. It is also possible to confine the significant range to $\theta$. FIG. 3A and FIG. 3B are respectively graphical representations showing the case where a reflective object is at rest and the case where it is moving.

In the description of this specification, by the suffix k, it means each time when the ultrasonic wave is repeatedly produced from all or part of the array of transducer elements Q at a prescribed interval and the suffix k relates to the time base. By the suffix m, it means each of outputs from the parallel beam forming device B on the basis of each of the reception ultrasonic wave beams $B_1, B_2 ... B_m ... B_M$ shown in FIG. 2, and the suffix m relates to the direction of arrangement of the transducer elements. In the following description, for brevity, the signal data line relating to k will be described in the form of the direction of the time base, or the k direction. With the signal data line as well relating to m, for brevity, it will be described in the form of the direction of arrangement of the transducer elements, or the m direction.

Figure 4:
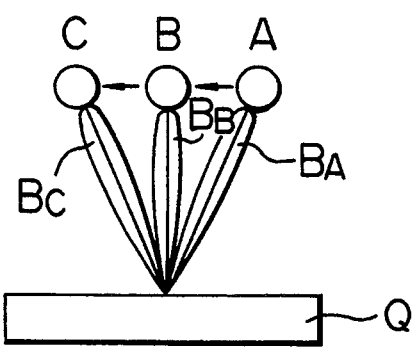
Figure 5:
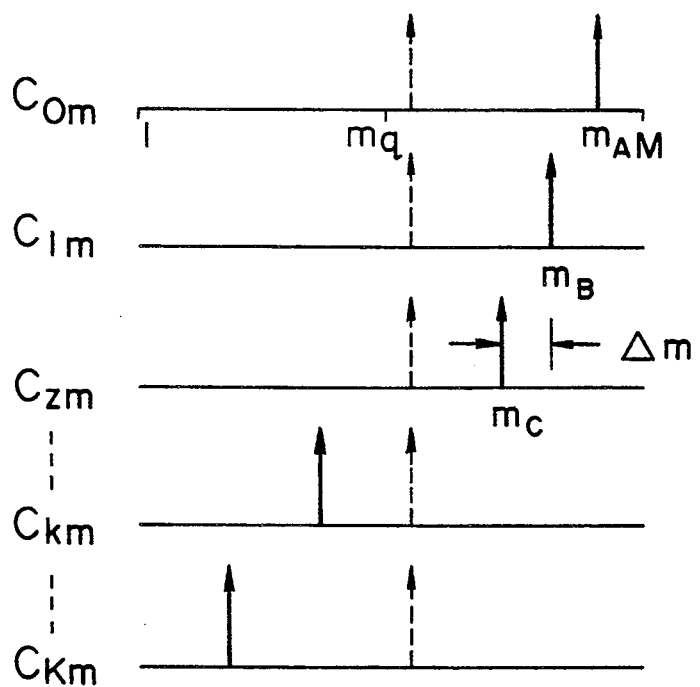
Figure 6:
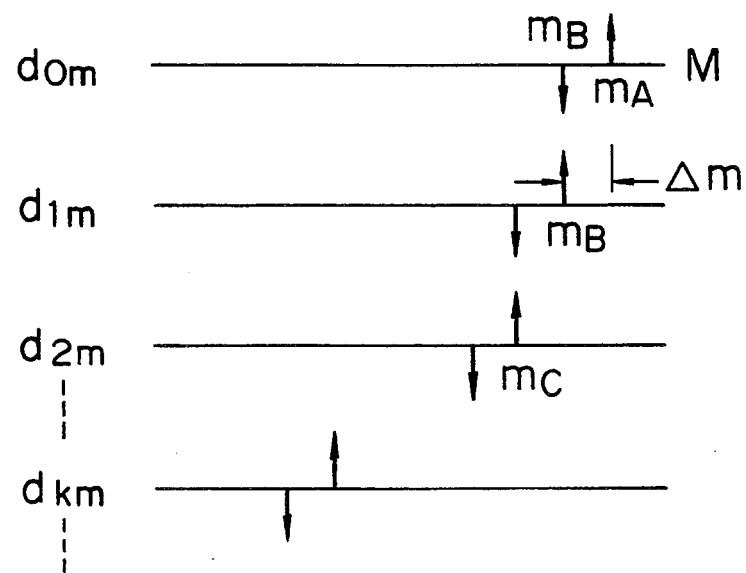

In the case where a reflective object at point P is quiescent, the signal $b_{km}(t)$ appears as a reflection signal produced at the output of channel $m_p$ formed in the direction of P as shown in FIG. 3A, and the position of output channel is not varied by the number of repetitions of transmission. The time length since the transmission to the emergence of the reflection signal is the propagation time of the ultrasonic wave, and it is 2L/C where C is the velocity of sound. The ultrasonic wave is transmitted through the time positions represented by the striping k=0, k=1, ... and the reflected wave emerges in the time position of 2L/C. FIG. 4 is a view showing the state in which the reflective object moves in parallel to the position of Q. FIG. 5 and FIG. 6 are respectively views showing the signal processings for the movement of FIG. 4.

If the reflective object moves to positions A, B and C at transmission times $t_0$, $t_1$ and $t_3$, respectively, as shown in FIG. 4 in the direction parallel to Q, the reception signal $b_{km}(t)$ varies in channel of emergence of reflection signals as indicated by $m_A$, $m_B$ and $m_C$ in FIG. 3B. By measuring the amplitude and phase of $b_{km}(t)$ at time points $t_e(t_e=2L/C)$ of emergence of reception signals and evaluating them as complex values $C_{km}$, these values are plotted with respect to the beam positions m as shown in FIG. 5. That is, in FIG. 5, the complex value corresponding to the reception signal is moved successively from the right-hand side position $m_A$ towards the left-hand side through the central position $m_q$. In this connection, $C_{km}$ can be regarded as the function of m, i.e., the relationship of $C_{km}=C_k(m)$ is established. Then, it is assumed that the amounts of movement of the lateral direction is $\Delta m$ for each transmission, the channel is m and the number of transmissions is k. Then, if the complex value $C_0(m)$ when k=0 is used, FIG. 5 reveals the following relation.

$$C_{km}=C_0(m+k\Delta m) \quad (1)$$

For the amplitude $b_{km}$ and phase $\phi_{km}$ of the reception signal $\hat{b}_{km}(te)$ at time $t_e$, the $C_{km}$ is expressed based on FIG. 3B as:

$$C_{km}=\hat{b}_{km}\cdot e^{j\phi_{km}}=\hat{b}_{km}\cdot e^{j\phi} \quad (2)$$

and the movement of the case of FIG. 4 results in the same phase for all positions.

Components indicated by the dashed arrows in FIG. 5 are reflection signals from a quiescent object and they do not move. Accordingly, by conducting the differential process between adjacent signals in the same channel at each repetitive transmission, e.g., between $C_{1m}$ and $C_{2m}$, between $C_{2m}$ and $C_{3m}$, and so on, the moving target indication is achieved. Namely, the differential process produces an output $d_{km}$ ($d_{km}=C_{km}-C_{(k+1)m}$) as shown in FIG. 6, and the signals created by the quiescent object are removed.

Figure 7:
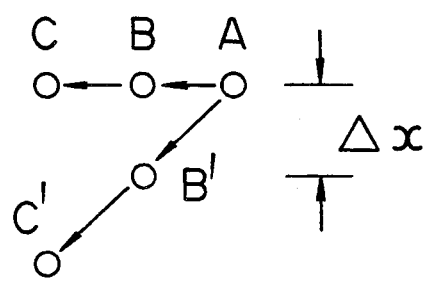
Figure 7:
Figure 8:
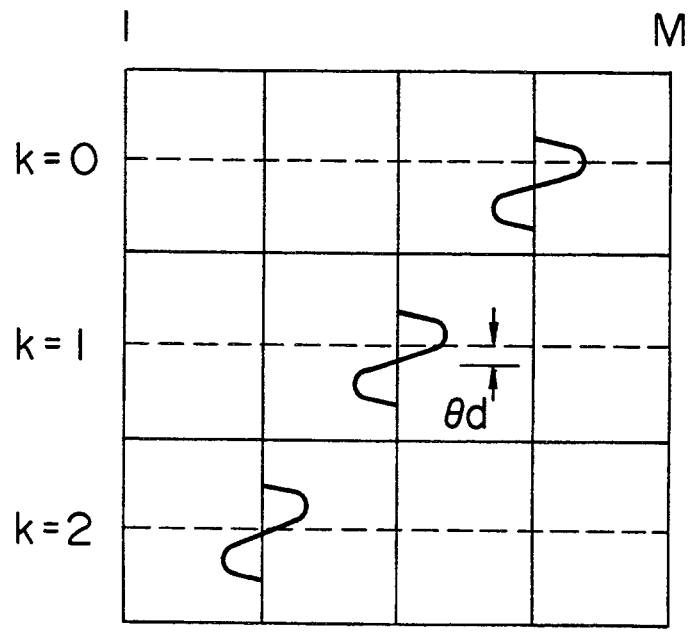

FIG. 7 and FIG. 8 are respectively views showing a direction of movement and a reflection waveform in the case where the reflective object is moved diagonally with respect to Q.

Although a complete transverse movement of a target is assumed in FIG. 4 for simplicity, it is accompanied by the movement in the depth direction in most practical cases as shown in FIG. 7, and the target moves to position B' at time point $t_1$ and to position C' at $t_2$ for example. In such a case, the signal has its phase at time point $t_e$ varying with the immediate distance to the reflective object as shown in FIG. 8. That is, at the position indicated by the dashed line of k=0, the signal has its phase leading by ¼ of the wavelength, in the position indicated by the dashed line of k=1, it has its phase leading by ⅜ of the wavelength, and in the position indicated by the dashed line of k=2, the phase is leading by ½ of the wavelength. The amount of variation $\phi_d$ is evaluated in terms of the axial velocity component Vr as:

$$\theta_d = 2\left(\frac{2\pi}{\lambda}\right)\Delta x = \frac{4\pi}{\lambda} Vr \cdot t_0 \quad (3)$$

where $\lambda$ is the wavelength, $t_0$ is the transmission interval ($t_0=t_{k+1}-t_k$), and $\Delta x$ is the distance of movement in the depth direction. Accordingly, when the $C_{km}$ is expanded to general movements represented by $\tilde{C}_{km}$, it is given as:

$$\tilde{C}_{km}=C_{km}\cdot e^{jk\theta_d} \quad (4)$$

and, in this case, the differential process output $d_{km}$ is as follows.

$$\begin{aligned}
\tilde{d}_{km} &= \tilde{C}_{km} - \tilde{C}_{(k+1)m} \\
&= C_{km} \cdot e^{jk\theta d} - C_{(k+1)m} \cdot e^{jk(k+1)\theta d} \\
&= \{C_{km} - C_{(k+1)m} \cdot e^{j\theta d}\} e^{jk\theta d} \\
&= \{C_0(m + k\Delta m) - C_0[m + (k+1)\Delta m] e^{j\theta d}\} e^{jk\theta d} \\
&= d_\theta \Delta(m + k\Delta m) e^{jk\theta d}
\end{aligned} \quad (5)$$

where $$d_{\theta\Delta}(m) = C_0(m) - C_0(m + \Delta m)e^{j\theta d}$$

$$C_0(m) = C_{0m}$$

The positions of emergence of the $\tilde{d}_{km}$ in direction m are the same as shown in FIG. 6. The amount of movement $\Delta m$ in direction m in FIG. 6 is in correspondence to the target velocity $V\phi$ in the transverse direction as follows.

$$V\psi = \frac{\Delta m \cdot \epsilon \cdot L}{t_0} \quad (6)$$

By conducting the Fourier transformation for the $d_{km}$ in direction m, which is the direction of alignment of reception beams, the result $\tilde{D}_k(\sigma)$ is given as follows.

$$\begin{aligned}
\tilde{D}_k(\sigma) &= \sum_{m=1}^{M} d_{\theta\Delta}(m + k\Delta m) e^{jk\theta d} \cdot e^{-j\sigma m} \\
&= e^{jk\theta d} \cdot e^{jk\sigma\Delta m} \cdot D_{\theta\Delta}(\sigma) \\
&= e^{jk(\theta d + \sigma\Delta m)} \cdot D_{\theta\Delta}(\sigma)
\end{aligned} \quad (7)$$

where $D_{\theta\Delta}(\sigma)$ represents the Fourier transformation of $d_{\theta\Delta}(m)$ as follows.

$$D_{\theta\Delta}(\sigma) = \sum_{m=1}^{M} d_{\theta\Delta}(m) e^{-j\sigma m} \quad (8)$$

Another Fourier transformation for the $\tilde{D}_k(\sigma)$ on k, i.e., the direction of repetitive transmission yields $D(\sigma,\rho)$ as follows.

$$\begin{aligned}
\tilde{D}(\sigma,\rho) &= \sum_{k=1}^{K} \tilde{D}_k(\sigma) \cdot e^{-jk\rho} \\
&= D_{\theta\Delta}(\sigma) \sum_{k=1}^{K} e^{jk(\theta d + \sigma\Delta m - \rho)} \\
&= D_{\theta\Delta}(\sigma) E(\sigma,\rho)
\end{aligned} \quad (9)$$

Figure 9:
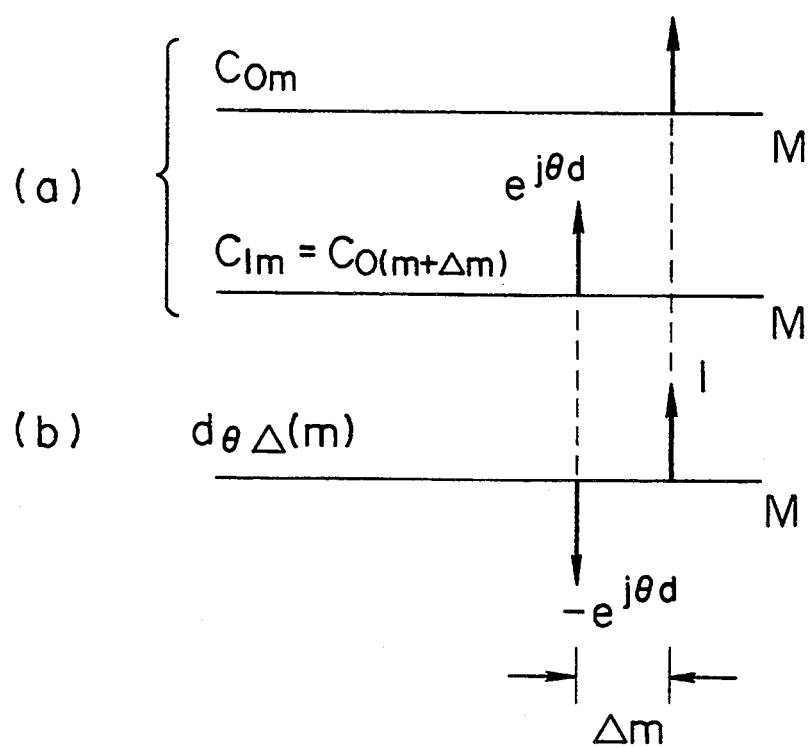
Figure 10:
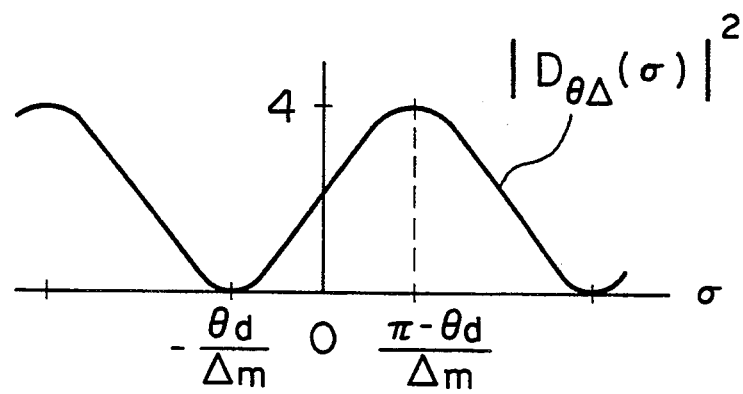
Figure 11:
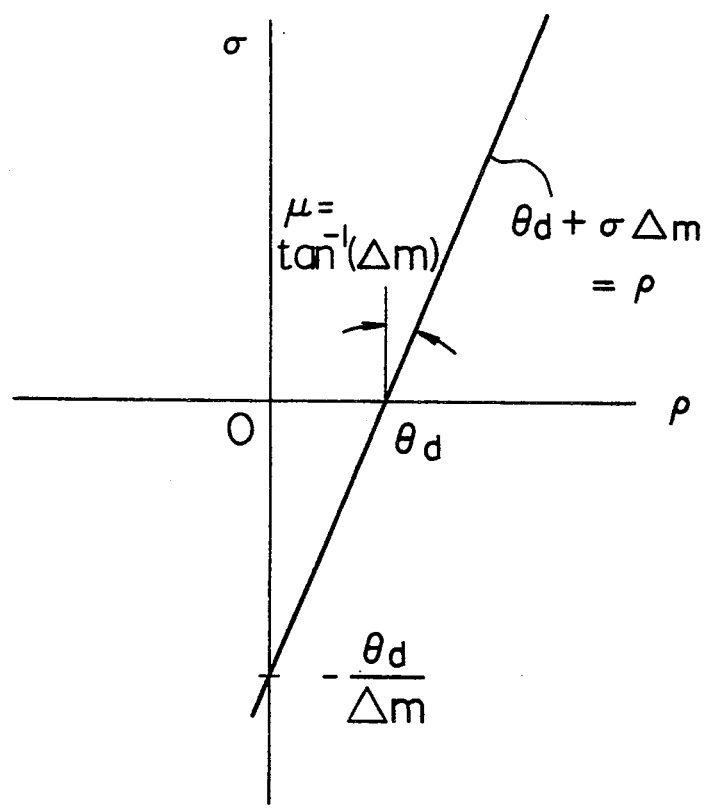

FIG. 9, FIG. 10 and FIG. 11 are respectively a view showing complex values and differential processing result, a view showing a power spectrum, and a graphical representation showing a cumulative term E of the differential processing result subjected to the Fourier transformation.

The $D_{\theta\Delta}(\sigma)$ is the result of Fourier transformation for the $d_{\theta\Delta}(m)$ which varies from $C_{0m}$ and $C_{1m}$ shown by (a) in FIG. 9 to that shown by (b) in FIG. 9. That is, since $C_{0m}$ has its amplitude of 1 in the channel m and $C_{1m}$ has its amplitude of $\exp(j\theta d)$ at the position where the amounts of movement $\Delta m$ is added to the channel m, the differential processing output thereof $d_{\theta\Delta}(m)(C_{0m}-C_{1m})$ has its amplitude which is obtained by subtracting the negative value of $(-\exp(j\theta_d))$ at the position $(m+\Delta m)$ from the positive value of 1 at the position m. This Fourier transformation results as follows.

$$D_{\theta\Delta}(\sigma) = 1 - e^{j(\sigma\Delta m + \theta d)} \quad (10)$$

It has a power spectrum of $|D_{\theta\Delta}(\sigma)|^2$ as follows.

$$|D_{\theta\Delta}(\sigma)|^2 = 2\{1 - \cos(\sigma\Delta m + \theta_d)\} \quad (11)$$

and it is as shown in FIG. 10. The power spectrum has, as shown in that figure, a peak value at position $(\pi - \theta_d)/\Delta m$, and this position moves in accordance with the transverse velocity $\Delta m$ and axial velocity $\theta_d$. The power spectrum has a null point at the position which meets $\sigma_0\Delta m + \theta_d = 0$, where $\sigma_0 = -\theta_d/\Delta m$.

Next, the terms of cummulative summation $E(\sigma,\rho)$ of the $\tilde{D}(\sigma,\rho)$ will be examined.

$$E(\sigma,\rho) = \sum_{k=1}^{K} e^{jk(\theta d + \sigma\Delta m - \rho)} \quad (12)$$

The above is generally the sum of irregular phase components, and is small in value.

The above expression (12) is generally the slum of irregular phase components to be small in value. This can be explained using the polar coordinates as follows. That is, since the velocity of movement of the reflective object has a constant value in each measurement point, the components of the velocity, i.e., $\Delta m$ and $\theta d$ are constant so that $k=1$, $k=2$ ... form vectors which rotate at equal interval angles. Accordingly, the sum of $k=1$, $k=2$ ... becomes zero.

$$\theta_d + \sigma\Delta m - \rho = 0 \quad (13)$$

In the above special case, it represents the sum of in-phase components, and $E(\sigma,\rho)$ has a large value. Therefore, when it is plotted on the $\sigma - \rho$ plane, it presents a large output only on a specific line as shown in FIG. 11. The gradient of the line relates to the transverse velocity $\Delta m(V\phi)$, and the intersection with the $\rho$ axis corresponds to the axial velocity $\theta_d(V_r)$.

Figure 12:
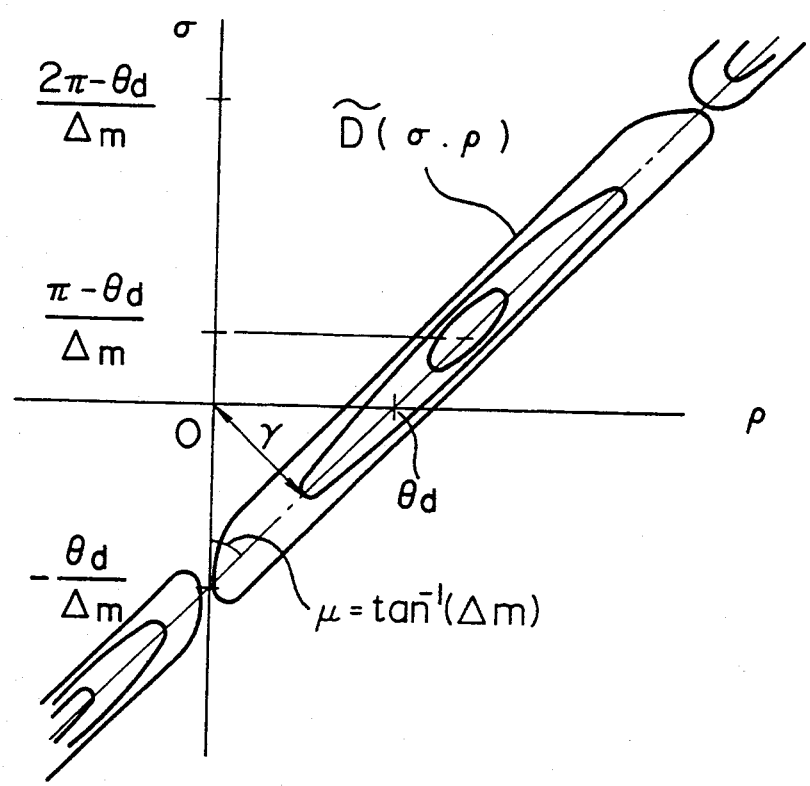
Figure 13:
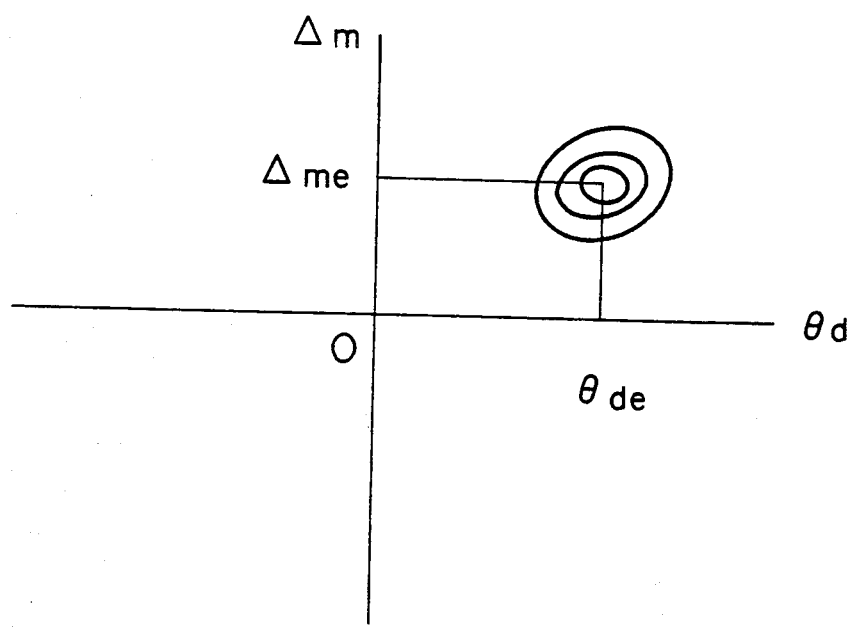

FIG. 12 is a plan view of $\tilde{D}(\sigma,\rho)$ which is obtained by subjecting the output of the differential processing to the Fourier transformation two times. FIG. 13 is a plan view relating to the transverse velocity and the axial velocity of the reflective object. From the above explanation, the $\tilde{D}(\sigma,\rho)$ which is given as a product of the $D_{\theta\Delta}(\sigma)$ and $E(\sigma,\rho)$ is as shown in FIG. 12, and by using the $\Delta m$ and $\theta_d$ measured on the diagram, the transverse velocity $V_\phi$ and axial velocity $V_r$ of the reflective object are measured independently to present its vectorial velocity.

$$\sigma_0 = -\theta_d/\Delta m \quad (14)$$

$$\theta_d + \sigma_0\Delta m - \rho_0 = 0 \quad (15)$$

With the relation pertinent to the null point of the $D_{\theta\Delta}(\sigma)$ given by equation (14) and the relation pertinent to the maximum value of the $E(\sigma,\rho)$ given by equation (15) being satisfied simultaneously, the $\rho_0$ becomes zero, and the null point of the $D_{\theta\Delta}(\sigma)$ at the position where the $E(\sigma,\rho)$ exists is as follows.

$$\sigma = -\theta_d/\Delta m$$

$$\rho = 0$$

Accordingly, the null point always exists on the intersection of the line of $\theta_d + \sigma\Delta m - \rho = 0$ and the axis of $\rho = 0$, as shown in FIG. 12.

The $D_{\theta\Delta}(\sigma)$, which is also a function of the $\theta_d$ and $\Delta m$, is determined uniquely from the values of $\theta_d$ and $\Delta m$. On this account, in the vicinity of the line given by the equation (16), on which the $E(\sigma,\rho)$ exists, the convolution of the $\tilde{D}(\sigma,\rho)$ and the known function $D_{\theta\Delta}(\sigma)$ is conducted to perform the optimizing filtering process thereby to obtain the detection output which provides the maximum signal-to-noise ratio as a function of the $\theta_d$ and $\Delta m$ corresponding to the target velocity.

$$\theta_d + \sigma\Delta m - \rho = 0 \tag{16}$$

Then, the optimizing filtering processing is conducted using the matched filter. In the case where an integration is performed along each straight line extending on the plane in FIG. 12, the curve of the power spectrum as shown in FIG. 10 rides on the straight line, and therefore, in the portion of the spectra curve where the power is low, an integration is conducted with its weight being lowered in order to reduce the noise.

Integration is conducted on the line for the sake of simplicity as follows.

$$R(\theta_d, \Delta m) = \int_{-\infty}^{\infty} D_{\theta\Delta}(\sigma) D(\sigma,\rho) d\sigma \tag{17}$$

$$= \int_{-\infty}^{\infty} D_{\theta\Delta}(\sigma) D(\sigma, \theta_d + \sigma\Delta m) d\sigma$$

where $$\rho = \theta_d + \Delta m$$

The result gives a peak value at the position corresponding to the target velocity as shown in FIG. 13. The values of $\theta_{de}$ and $\Delta_{me}$ which provide this position are the measured values representing the lateral and axial velocities.

Since this method is based entirely on the linear process, when the target velocity is distributed, the $R(\theta_d, \Delta)$ is distributed by itself in correspondence to the distribution of the flow rate.

The resolution of the present method, particularly the directional resolution is higher when the $\epsilon$ is smaller and $\theta$ is larger. Namely, when a larger number of reception signals are used, the better velocity resolution is obtained. On this account, it is desirable to make the exposure range of the ultrasonic wave wider and each reception beam formed on B narrower. An effective manner to meet these conditions is to make the transducer aperture smaller than the total aperture used for the reception.

It is effective for the axial resolution of the present method to make the interval of repetition of the transmission of the ultrasonic wave larger thereby to increase the number of repetition of transmissions.

The preferred embodiments of the present invention will hereinafter be described in detail with reference to FIG. 14 through FIG. 19.

Figure 14:
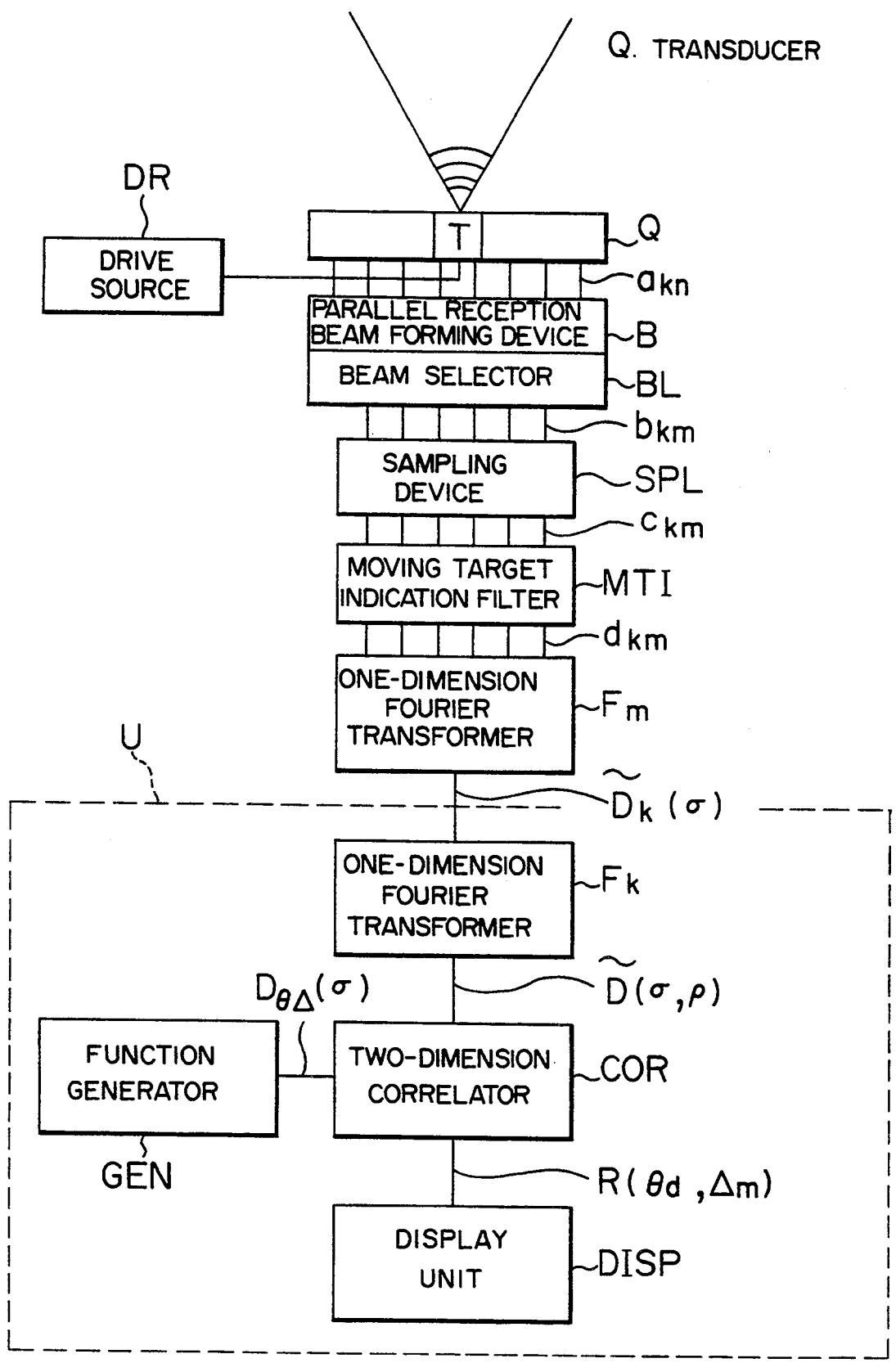

Indicated by Q in FIG. 14 is a transducer made up of N pieces of arrayed elements. Part T of the elements are driven by a drive source DR so that a pulsed ultrasonic wave is transmitted repeatedly at a transmission interval of $t_R$ to a wide space (in the angle $\theta$ shown in FIG. 2 or more).

In the arrangement of the embodiment of FIG. 14, the 64 transducer elements are arrayed with a pitch of 0.25 mm. Out of them, the two elements are driven. Then, the ultrasonic wave with a frequency of 3.5 MHz is transmitted repeatedly 20 times at a transmission interval of 1 msec to a wide space having an angle of 36 degrees larger than $\theta = 30$ degrees of the attention region so that a beam selector BL receives reception signals $b_{km}$ (k=1, 2 to 20; m=1, 2 to 30) within the range of the angle $\theta = 30$ degrees. Then, the suffix k indicates the number of transmission of interest based on the count of repetitive transmissions.

A reflection signal from a target derived from the transmitted ultrasonic wave is received by the transducer Q, and resulting signals of N in number are processed by a parallel reception beam forming device B, which produces reception signals in correspondence to ultrasonic beams. The parallel reception beam forming device may be formed of a parallel integration of well-known beam forming devices which delay signals of transducer elements individually and sum the signals thereby to produce reception signals for the reception beams having directivities in desired directions. The beams have a directional difference by an angle of $\epsilon$ between adjacent ones as shown in FIG. 2.

In the present embodiment, the beams have a virtually equal focal depth in order to accomplish high accuracy flow rate measurement for a specific depth. The beam selector BL selects reception signals $b_{km}(t)$ (where m=1 to M) of M in number, which represent reception beams of M in number within the range of the angle $\theta$ as shown in FIG. 2, from among the reception signals. The suffix k indicates the reception signal number based on the count of repetitive transmissions. The variable t indicates the time length expended since transmission.

The signals are sampled by a sampling device SPL and stored. The SPL output $C_{km}$ for each transmission and reception is assumed to be a function of time, and reflection signals from fixed objects are suppressed by means of a moving target indication filter MTI which performs a differential process on k among a plurality of data having the same value of t. The MTI output $d_{km}$ is treated as a function of m, and it is rendered Fourier transformation by a one-dimension Fourier transform device $F_m$. The output $\tilde{D}_k(\sigma)$ of the $F_m$ is rendered Fourier transformation as a function of k by a similar one-dimension Fourier transform device $F_k$ in a travel velocity analyzing device u to obtain $\tilde{D}(\sigma,\rho)$. The $\tilde{D}(\sigma,\rho)$ presents the intensity distribution as shown in FIG. 12 on the $\sigma-\rho$ plane, as has been explained in connection with the formulas (9) to (13), and reveals the axial velocity component $\theta_d$ of a moving object from the $\rho$-cut of the line appearing on the distribution and the transverse velocity component $\Delta m$ from the gradient of the line. Although the output $\tilde{D}(\sigma,\rho)$ of the Fourier transform device $F_k$ may be displayed on a two-dimensional plane, the present embodiment further proceeds to the calculation of a two-dimensional correlative function $R(\theta_d, \Delta)$ between the $\tilde{D}(\sigma,\rho)$ and $D_{\theta\Delta}(\sigma)$ given to all velocity components by means of a two-dimension correlation device COR. Indicated by GEN is a function generator which generates $D_{\theta\Delta}(\sigma)$ in correspondence to values of $\theta_d$ and $\Delta m$. The position $(\theta_{de}, \Delta_{me})$ of the peak value of the $R(\theta_d, \Delta m)$ represents the lateral velocity $V_\phi$, and axial velocity $V_r$ of the moving target, as has been explained in connection with FIG. 13. The display unit DISP displays the $R(\theta_d, \Delta m)$ on the two-dimension plane or reads out the measured value of the position $(\theta_{de}, \Delta_{me})$ of the peak value of the $R(\theta_d, \Delta m)$. These are the basic arrangement of the embodiment shown in FIG. 14.

FIG. 15 is a block diagram showing a modification of the embodiment of FIG. 14. The beam forming process by the parallel reception beam forming device B in FIG. 14 is known to be a Fourier transformation respecting to the space. Accordingly, it is possible to replace the B in FIG. 14 with a one-dimension Fourier transform device $F_\theta$. In this case, the Fourier transformation process is generally conducted for sampled values, and a sampling device SPL which samples the reception signals and stores the signals is placed in front of the one-dimension Fourier transform device $F_\theta$ as shown in FIG. 15. That is, the arrangement of FIG. 15 is designed in such a way that reception signals $a_{nk}(t)$ of transducer elements of N in number are sampled by the sampling device, and are rendered the Fourier transformation with $F_\theta$ in direction n and conducted through the beam selector BL, thereby producing outputs which are equivalent to the outputs $C_{km}$ of the sampling device SPL in FIG. 14. In FIG. 15, the arrangement of the velocity analyzing device U in the rear of the one-dimension Fourier transform device $F_m$ and one-dimension Fourier transform device $F_k$ is identical to that of FIG. 14.

Figure 16:
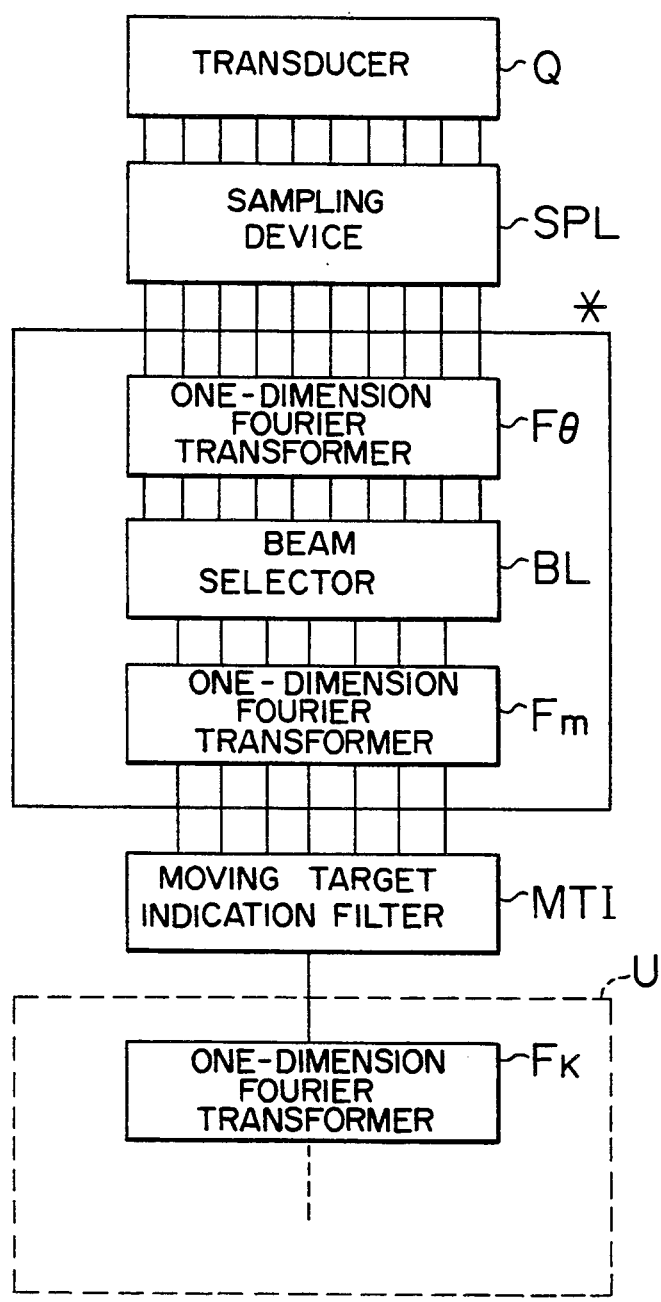

FIG. 16 is a block diagram showing still another modification of FIG. 15.

Figure 17:
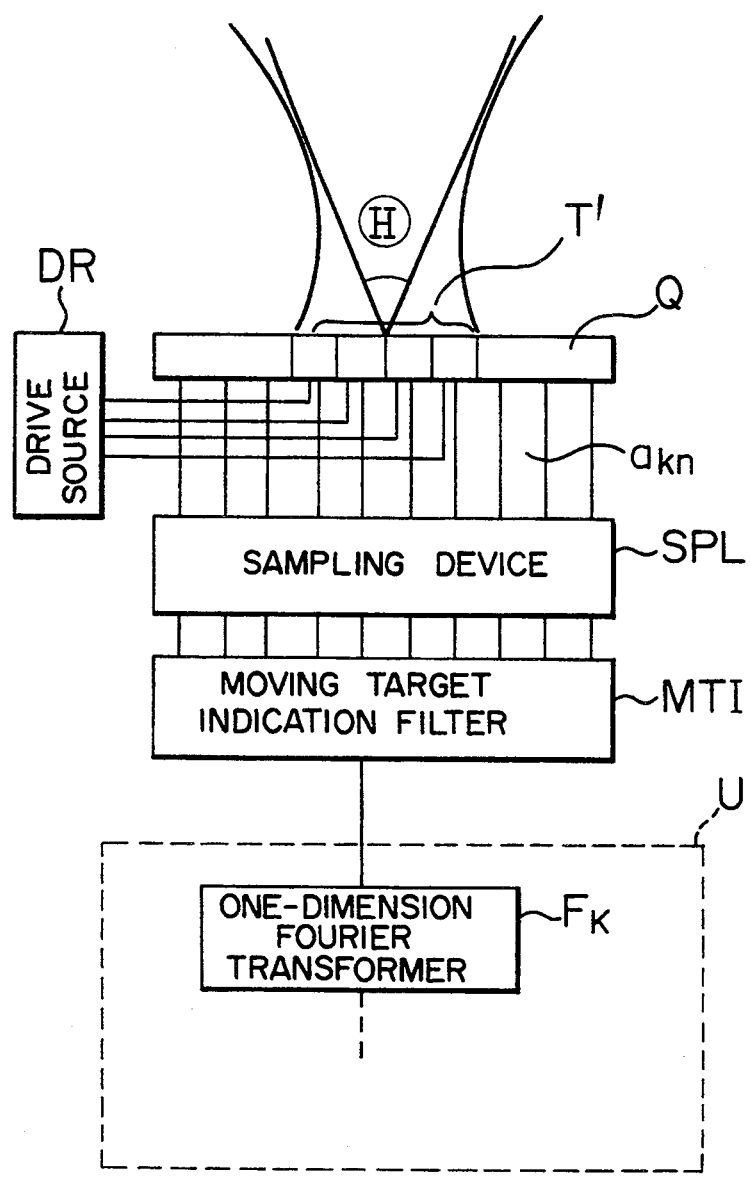

The MTI process of FIG. 15 has no difference before and after the process by the $F_m$. Accordingly, even with the one-dimension Fourier transform device $F_m$ being connected to the front stage of the moving target indication filter MTI as shown in FIG. 16, the same operation as of the case of FIG. 15 takes place. It will be appreciated from this figure that the section marked by "*" in FIG. 16 is Fourier transformation for twice and it has basically identical to no operation, but merely confines the area of attention to the range of the angle $\theta$ using the BL. FIG. 17 is a block diagram showing yet another modification of FIG. 16. From the above description, the embodiment of FIG. 17 is simply arranged in such a way as to include only the array of transducer elements Q, the sampling device SPL, the moving target indication filter MTI and the travel velocity analyzing device U by removing the sections marked by "*" in FIG. 16. In this case, the function of the beam selector BL can be removed by carrying out another method. That is, partial element group T' among the transducer elements are activated to transmit the ultrasonic wave to the region $\theta$ and the reflection signals from this region are received, as shown in FIG. 17, whereby the beam selector BL can be eliminated.

In the arrangement of the embodiment of FIG. 17, the 32 transducer elements are arrayed with a pitch of 0.25 mm. Out of them, only two elements are driven. Then, the ultrasonic wave with a frequency of 3.5 MHz is transmitted repeatedly 10 times at a transmission interval of 1 msec to the wide space of the attention region $\theta = 30$ degrees so that the reception signals $a_{kn}$ (k=1, 2 to 10; n=1, 2 to 32) from the range of the angle $\theta = 30$ degrees are obtained. Then, the suffix k indicates the number of transmission of interest based on the count of repetitive transmissions.

The arrangement of FIG. 17 is designed in such a way that the reception signals $a_{k1}, \ldots, a_{kN}$ from the transducer elements sampled by the sampling device SPL are introduced to the moving target indication filter MTI, and the outputs of the MTI are directly introduced to the one-dimension Fourier transform device $F_k$ in the block U. Although the measurement result by this arrangement also becomes the same as that of FIG. 12, in the present embodiment, the reception elements are disposed on the axis of ordinate.

Figure 18:
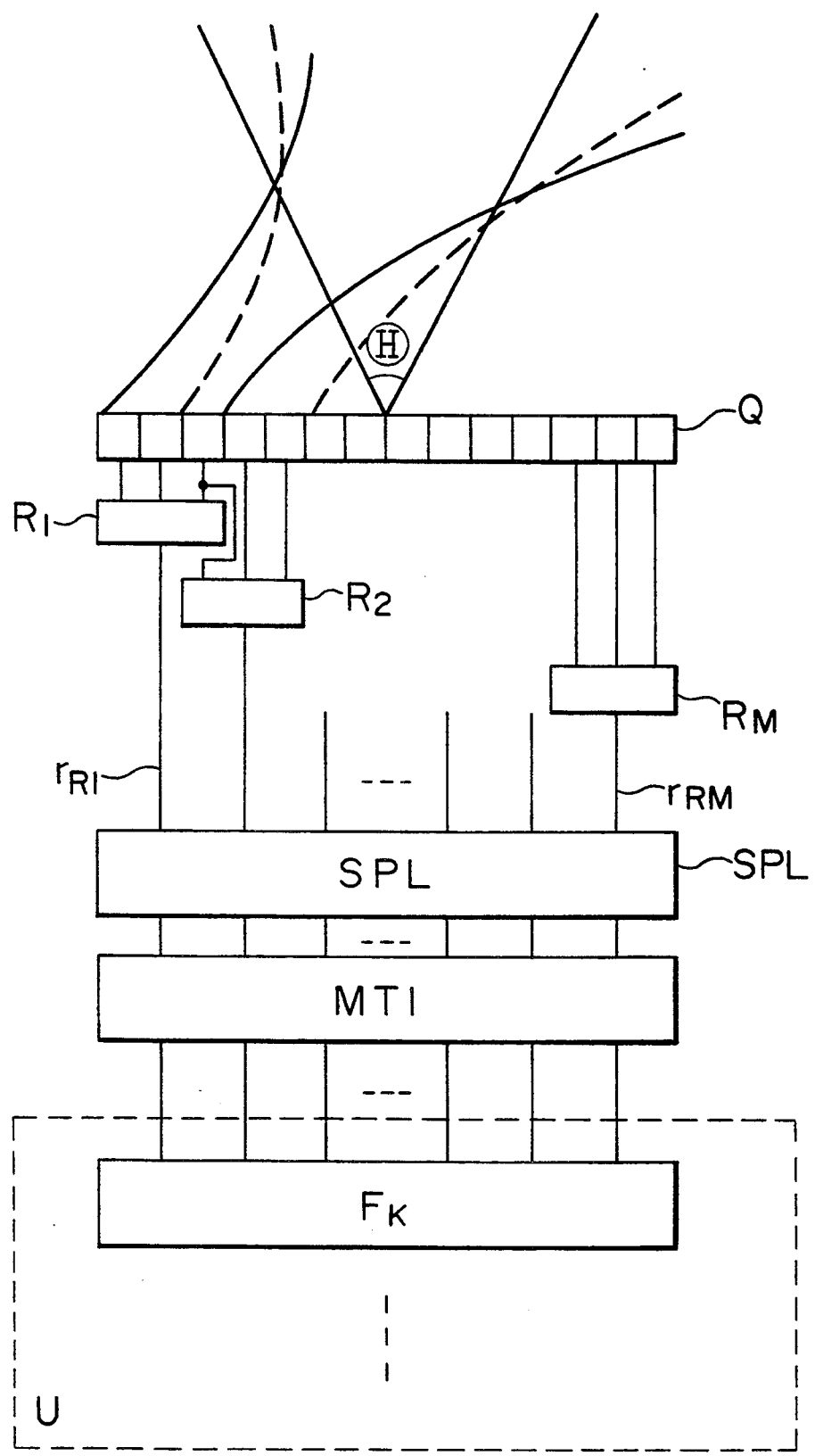

FIG. 18 is a block diagram showing the arrangement of another modification of FIG. 17. The arrangement is, as shown in FIG. 18, may also be designed in such a way that the reception signals $a_{k1}, \ldots, a_{kN}$ from the transducer elements are divided into groups through partial apertures, with these groups being connected to respective beam forming phasing devices $R_1, \ldots, R_M$ for implementing the beam forming operation, and outputs $r_{R1}, \ldots, r_{RM}$ indicative of a plurality of beams in the range of the region $\theta$ are sampled with the sampling device SPL in the same manner as in the case of FIG. 17 before conducting the successive processing.

In the arrangement of the embodiment of FIG. 18, the 64 transducer elements are arrayed with a pitch of 0.25 mm. In this connection, the array of transducer elements are divided into 16 groups. Then, the ultrasonic wave with a frequency of 3.5 MHz is transmitted repeatedly 10 times at a transmission interval of 1 msec so that the reception signals $b_{km}$ (k=1, 2 to 10; m=1, 2 to 16) are obtained in the space of the attention region $\theta = 30$ degrees. The suffix k indicates the number of transmission of interest based on the count of repetitive transmissions.

Also in the embodiments of FIGS. 16 through 18, the arrangement of the velocity analyzing device U which calculates the lateral velocity $V_{100}$ and distant velocity $V_r$ is completely identical to the embodiment of FIG. 14. The order of disposition of the arrangement can be changed arbitrarily. Moreover, instead of using the two-dimension correlator COR, the distribution of $\overline{D}(\sigma, \rho)$ may be displayed intact. Further, the SPL is arranged using a usual sample-holding circuit, A/D converter and the like, or a possible alternative arrangement is a sampling device of the type of phase comparison which performs multiplication with a reference signal and low band filtering, and an improved s/n is expected in this case.

Figure 19:
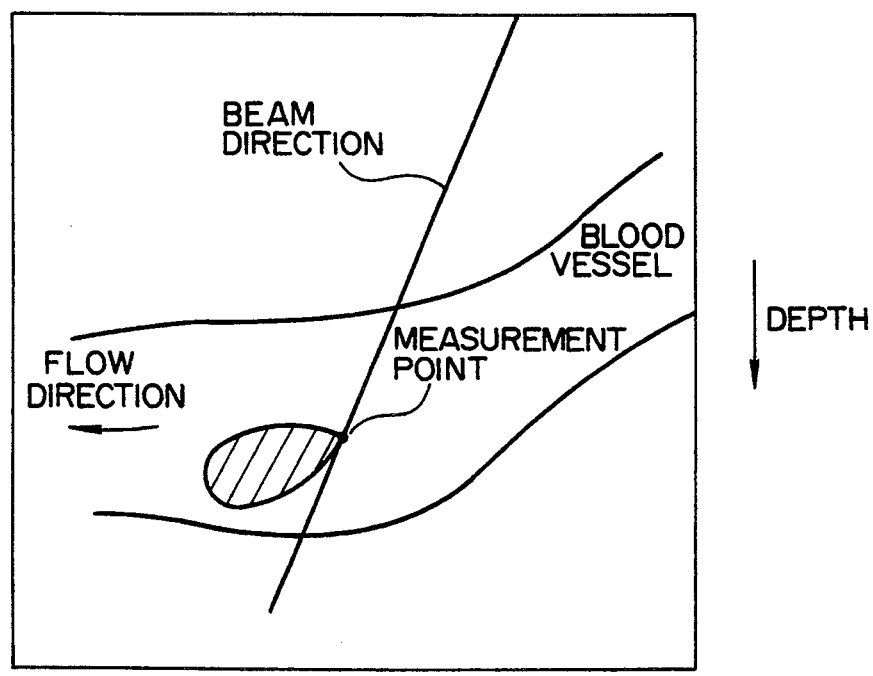
FIG. 19 is a diagram showing the concept of a display method as an example.
Figure 19:
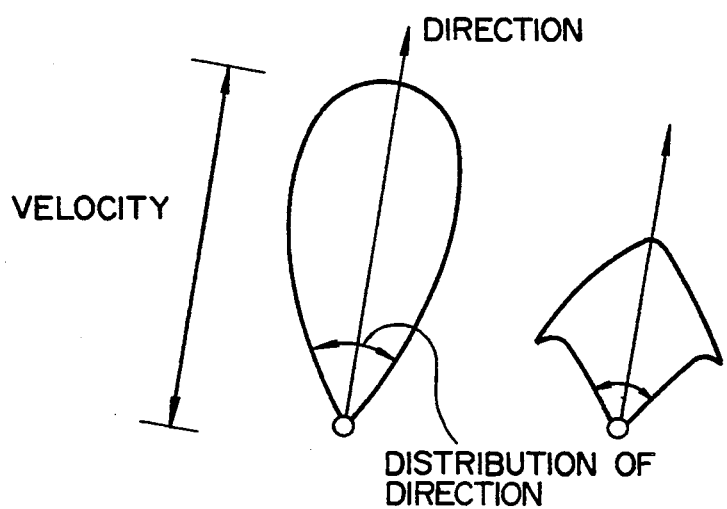

FIG. 19 is a view showing the flow of a blood flow in a live body. According to the embodiments shown in FIG. 14 through FIG. 18, since two-direction components of the velocity are obtained, for example, the direction, the flow rate and the distribution of directions of a blood flow in a live body are evaluated. Consequently, it also becomes possible to display a measurement point in the two-dimension tomograph plane and the flow rate, the direction and the distribution at the measurement point, as shown in FIG. 19.

In FIG. 19, with respect to the depth direction of the live body, there is shown the direction of the blood flow, the direction of the ultrasonic wave beam, and the measurement point.

The method of integrating $\overline{D}(\sigma, \rho)$ (shown in FIG. 12) obtained by subjecting the output of the differential processing to the Fourier transformation twice to produce the display in which the measurement result of large scale is outputted at the position corresponding to the velocity of the reflective object as shown in FIG. 13 is not limited to the correlation processing by the two-dimension correlator COR shown in FIG. 14.

Figure 20:
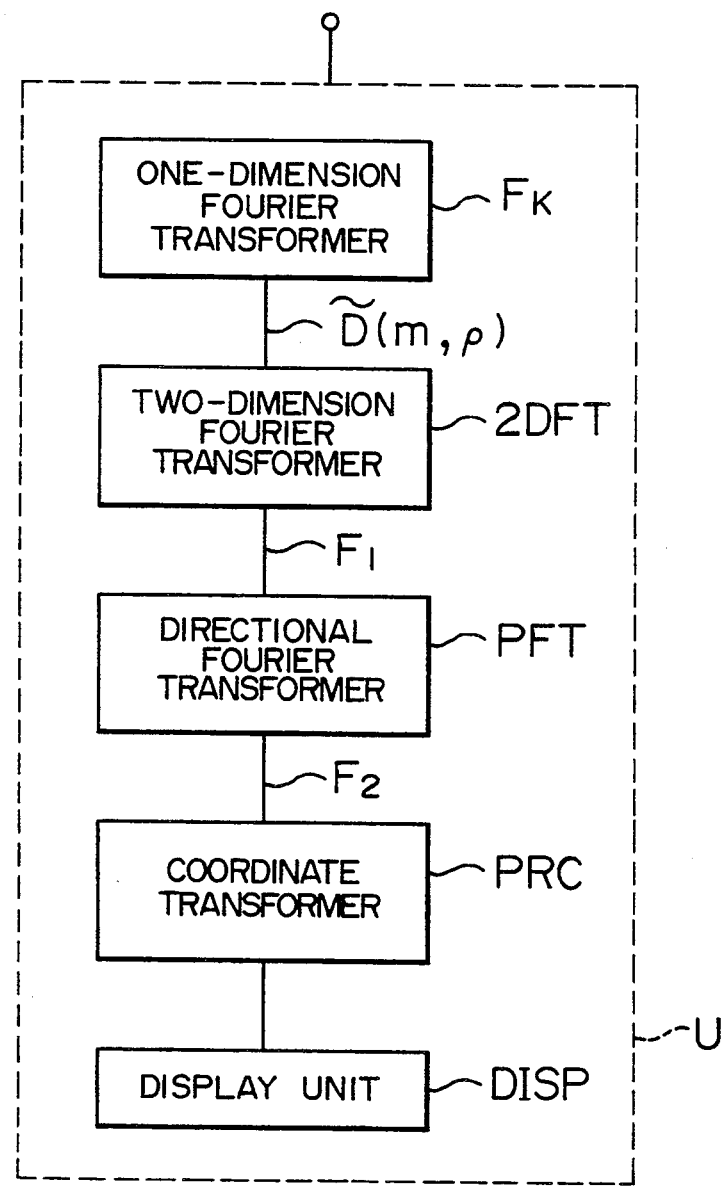
Figure 21A:
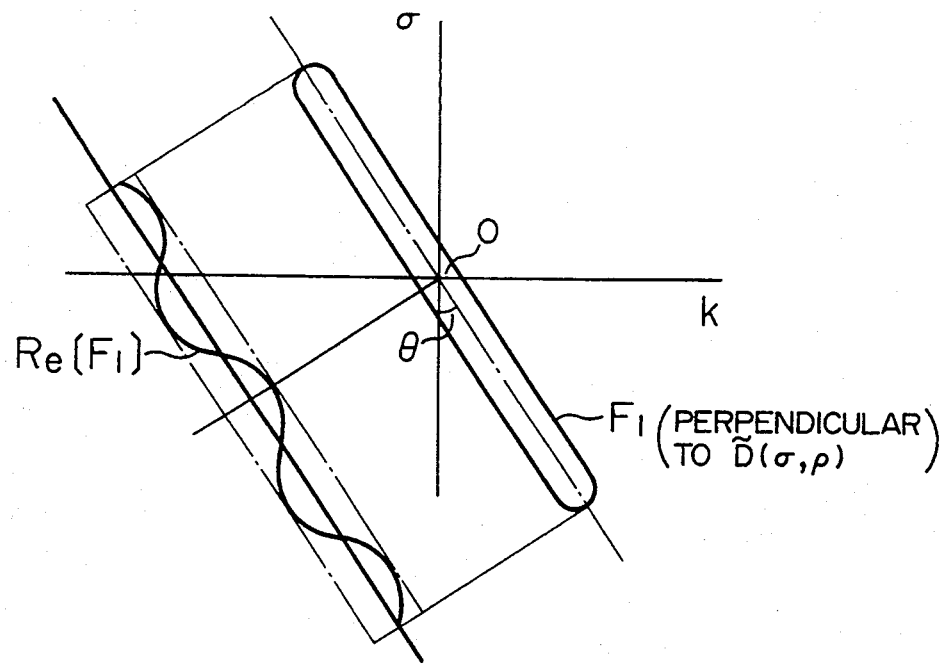
Figure 21B:
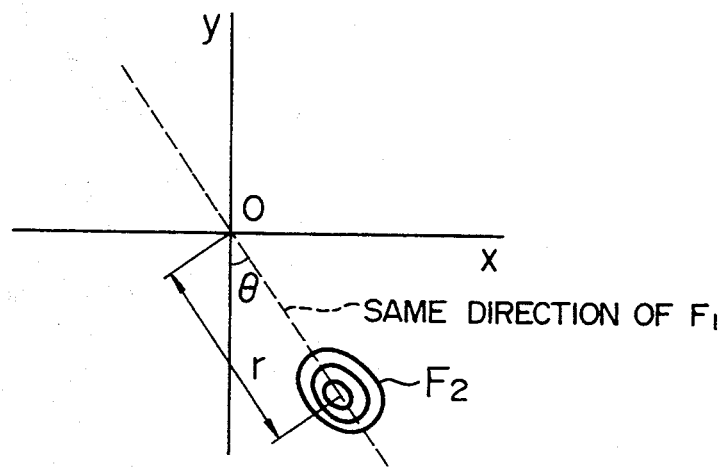
Figure 21C:
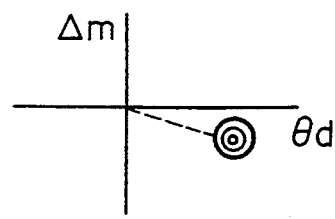

FIG. 20 is a block diagram showing the arrangement of the embodiment of the travel velocity analyzing device U, according to the present invention, employing another method. FIG. 21A, FIG. 21B and FIG. 21C are respectively views showing an output $F_1$ of a two-dimension Fourier transformer of FIG. 20, an output $F_2$ of a directional Fourier transformer of FIG. 20, and an example of coordinate transformation. The travel velocity analyzing device U is made up of a one-dimension Fourier transformer $F_k$, a two-dimension Fourier transformer 2DFT, a directional Fourier transformer PFT, a coordinate transformer PRC and an image display DISP. The one-dimension Fourier transformer $F_k$ subjects the outputs of the moving target indication filter MTI, which have been, for example, obtained from the arrangement of FIG. 17 or FIG. 18, to the Fourier transformation with respect to the direction of the time base (the k direction) thereby to obtain $\tilde{D}(m,\rho)$ which shows the result of the two-dimension Fourier transformation and is defined by treating the axis of ordinate in FIG. 12 as m. When the $\tilde{D}(m,\rho)$ is then subjected to the two-dimension Fourier transformation by the two-dimension Fourier transformer 2DFT with respect to the direction of the time frequency axis (the $\rho$ direction) and the direction of arrangement of the transducer elements (the m direction), it is transformed to the output distribution of straight line which coincides with the origin diagonally as shown in $F_1$ of FIG. 21A. this result will be readily understood by considering the relationship between a projected image in an X ray CT and a two-dimension Fourier transformation image.

The characteristic curve $F_1$ of FIG. 21A extends in a direction perpendicular to the $\tilde{D}(\sigma,\rho)$ shown in FIG. 12, and the amplitude of the straight line-like region is uniform but only the phase is changed. The phase rotation velocity is proportional to a distance $\gamma$ between the origin in FIG. 12 and the $D(\sigma,\rho)$. In FIG. 21A, there is shown the real number part $Re[F_1]$ of $F_1$ on the straight line coinciding with the origin. The characteristic curve $F_1$ of FIG. 21A is transformed to the characteristic curve $F_2$ shown in FIG. 21B by the directional Fourier transformer PFT shown in FIG. 20. That is, the directional Fourier transformer PFT carries out the Fourier transformation by treating the values on the straight line, which coincides at an angle of $\theta$ with the origin O in FIG. 21A, as a one-dimension sequence of numbers, and carries out such a processing with respect to each angle. Thus, since the Fourier transformation is carried out with respect to each of the inclined directions, there is obtained the display of contour which corresponds in direction to the direction of $F_1$ of FIG. 21A, and is distributed around the position apart from the origin O by a distance of r with making an angle $\theta$ with the Y axis, and has a large signal intensity. The distance r in FIG. 21B is a distance which is proportional to $\gamma$ in a direction of the angle corresponding to $\Delta m$. We can deduce the following relationships from FIG. 12 and FIG. 21A.

$$\Delta m = \tan\mu = \tan(\pi/2 - \theta)$$
$$\theta_d = \gamma \sqrt{(\Delta m)^2 + 1} = A \cdot r \sqrt{(\Delta m)^2 + 1}$$

(A: constant value)

Figure 23:
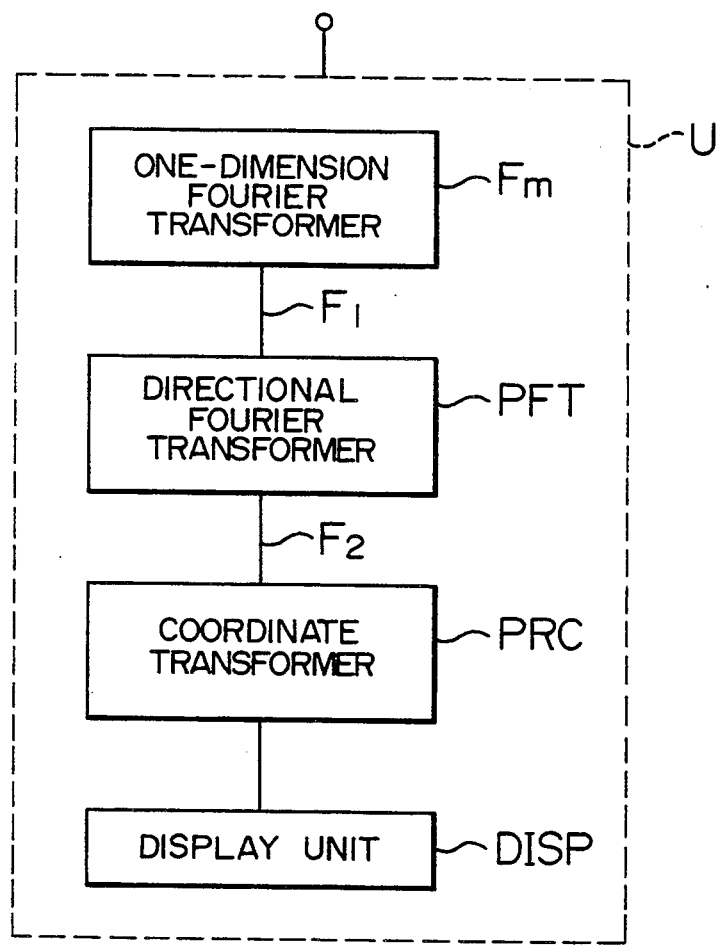

By means of the coordinate transformer PRC using the above relationships, it is possible to obtain the characteristic curve in the form of $(\theta_d, \Delta m)$ which is obtained by subjecting the characteristic curve in the form of $(r,\theta)$ of FIG. 21B to the coordinate transformation as shown in FIG. 21C, in the same manner as in the case of FIG. 23. Incidentally, the constant value A is determined by the arrangement factors of the system such as a frequency of the used ultrasonic wave, and an interval of arrangement of the transducer elements.

FIG. 22 is a view useful in explaining the arrangement equivalent to the Fourier transformation in FIG. 20. FIG. 23 is a block diagram showing the arrangement of the best target velocity analyzing device according to the present invention. The arrangements of the one-dimension Fourier transformer Fk and the two-dimension Fourier transformer 2DFT, shown in FIG. 20, become equal to that of one-dimension Fourier transformer Fm, as shown in FIG. 22. That is, since the two-dimension Fourier transformation is the combination of the k direction (the direction of time base) and the m direction (the direction of arrangement of the transducer elements), the processing by the one-dimension Fourier transformer Fk and the two-dimension Fourier transformer 2DFT becomes equivalent to the Fourier transformation of one time with respect to the direction by the one-dimension Fourier transformer Fm. As a result, the arrangement of the travel velocity analyzing device U shown in FIG. 20 can be simplified as shown in FIG. 23. That is, the travel velocity analyzing device U of FIG. 23 is made up of the one-dimension Fourier transformer Fm, the directional Fourier Transformer PFT, the coordinate transformer PRC and the image display DISP. After the output distribution of the straight line $F_1$ as shown in FIG. 21A has been obtained by the one-dimension Fourier transformer Fm, the transformation output $F_2$ as shown in FIG. 21B is obtained by the directional Fourier transformer PFT to be transformed to the coordinate of $(\theta d, \Delta m)$ as shown in FIG. 21C by the coordinate transformer PRC, so that the resulting data can be outputted to the image display DISP.

In the target velocity analyzing device of the present invention, the vectorial movement velocity of the blood flow is measured in such a way that the ultrasonic waves are transmitted from the transducer elements every time $t_k(k=0, 2, \ldots, K)$, the reception signals corresponding to the specific depth is subjected to the Fourier transformation with respect to the direction of arrangement of the transducer elements (the m direction) by the one-dimension Fourier transformer Fm, a plurality of frequency spectra as that result are produced in a time series manner corresponding to the transmission times $t_k(k=0, 2, \ldots, K)$ of the ultrasonic waves to consider the frequency spectra of the time and the result becomes a two-dimension signals, those two-dimension signals are disposed on the $(k,\sigma)$ coordinate, the values on each of the plural straight lines coinciding at respective angles with the origin of the $(k,\sigma)$ coordinate are subjected to the Fourier transformation by the directional Fourier transformer PFT with being treated as the one-dimension sequence of numbers, and the resulting data are transformed to the $(\theta_d, \Delta m)$ coordinate shown in FIG. 21 by the coordinate transformer PRC.

Figure 25:
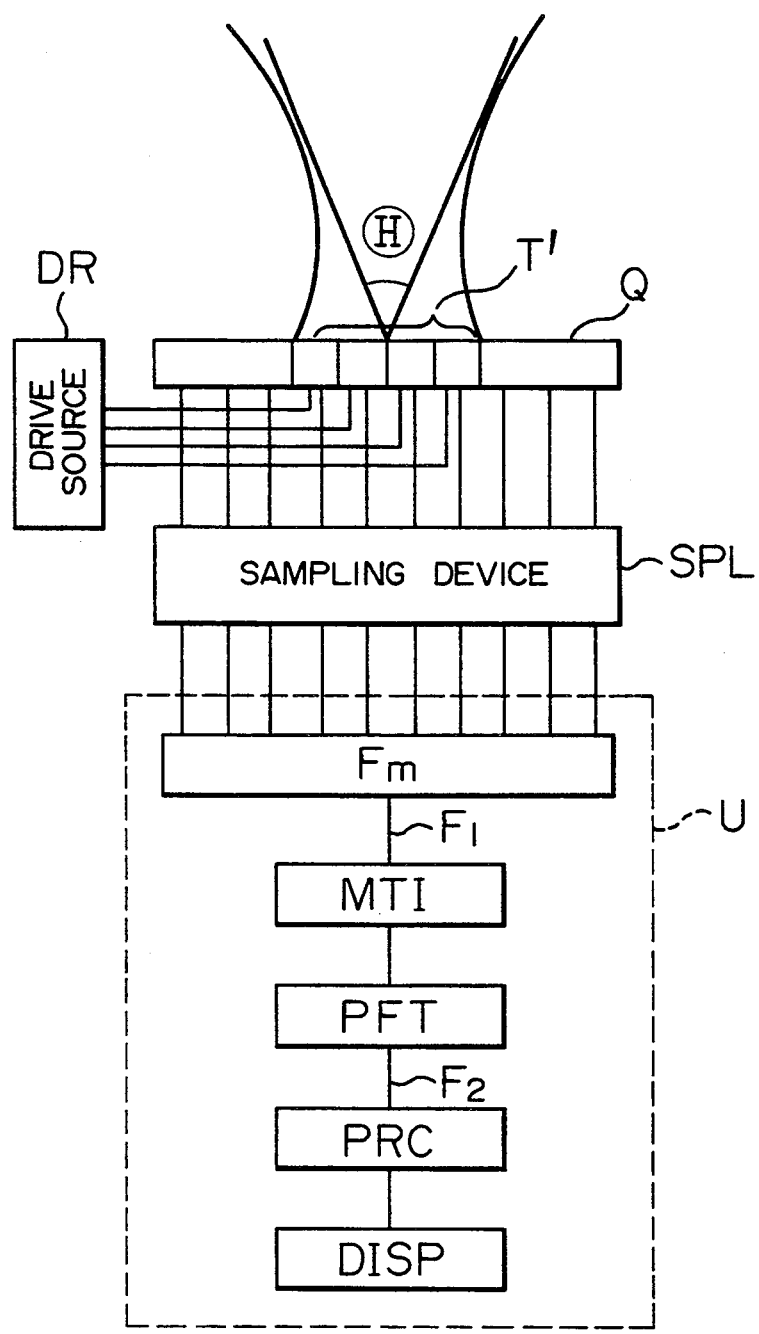
Figure 26:
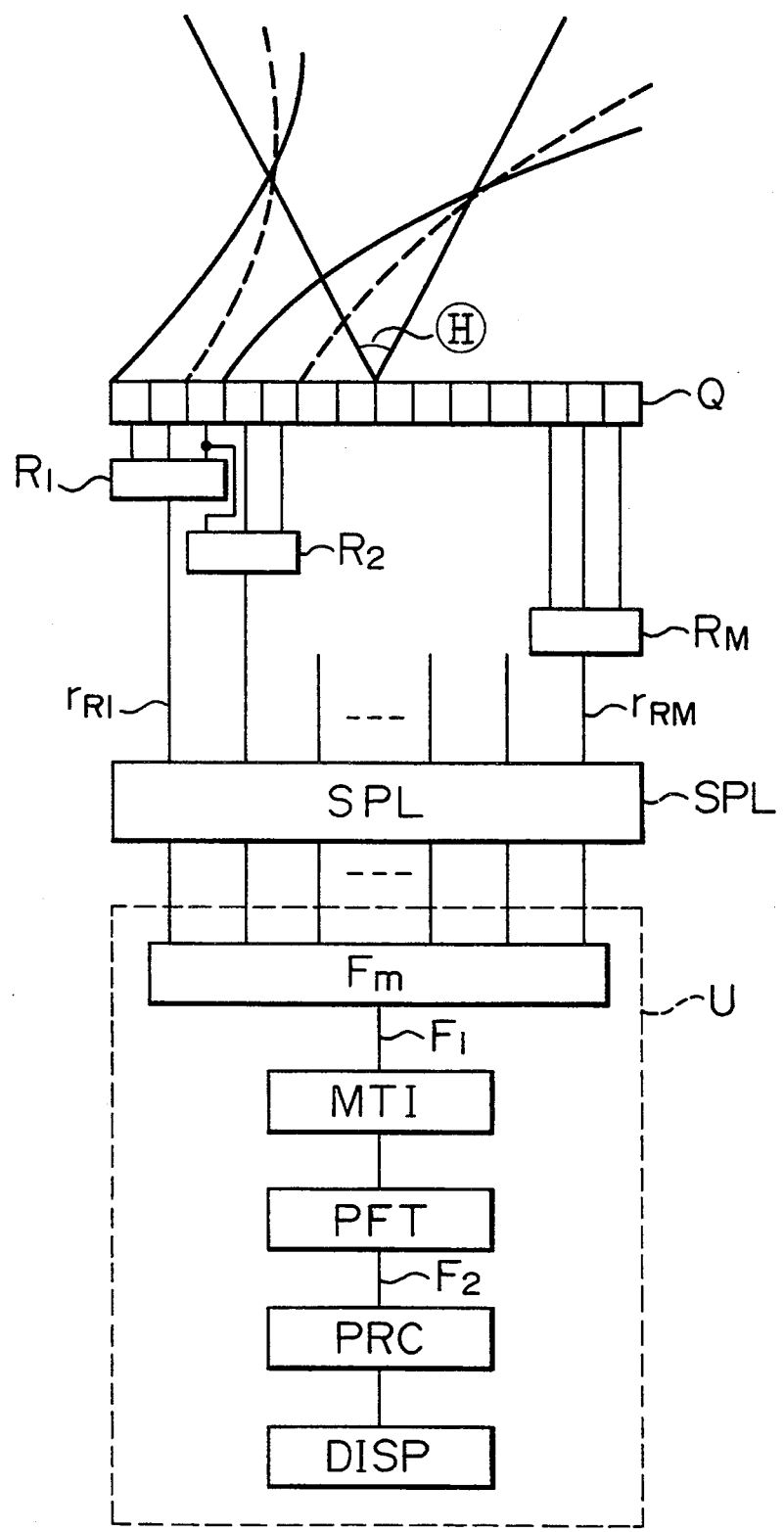

FIG. 24 is a block diagram showing the arrangement of the travel velocity analyzing device in which the moving target indication filter MTI is disposed in the rear stage of the one-dimension Fourier transformer Fm. As has been described hereinabove, the processing of the moving target indication filter MTI utilizes that there is no difference before and after the processing by the one-dimension Fourier transformer Fm. However, when the moving target indication filter MTI is disposed in the rear stage of the one-dimension Fourier transformer Fm, the signal can be obtained with the higher S/N ratio being provided. FIG. 25 and FIG. 26 are respectively block diagrams showing the arrangements of embodiments of the ultrasonic flowmeter employing the travel velocity analyzing device shown in FIG. 24. In each of the embodiments shown in FIG. 25 and FIG. 26, the conditions of transmission and reception of the ultrasonic wave (the attention region, the frequency, the transmission interval, the number of repetition of the transmissions, and the like), and the arrangement of the sampling device SPL are the same as those of the embodiments of FIG. 17 and FIG. 18.

In the embodiments as well shown in FIG. 25 and FIG. 26, it will be readily understood that the blood flow in the live body can be displayed.

As set forth in detail hereinabove, according to the present invention, it is possible to construct the ultrasonic flowmeter having a very simple construction, and since all of the processings are performed in the linear processing manner, when the velocity of the reflective object is distributed, the distribution can be measured, and even when the transverse velocity has the flow of positive direction and that of negative direction, both the flows can be measured. Of course, even in the case where there are a plurality of reflective objects, and they have different flow directions and velocity distributions, it is possible to measure the direction of flow and the velocity distribution every reflective object. Thus, the velocity of the reflective object can be measured as the vector quantity having its direction and magnitude irrespective of the direction of movement of the reflective object.

According to the present invention, in addition to the blood flow, any thing can be measured as long as it reflects the ultrasonic wave. Moreover, the present invention also is applicable to the navigation and the like.

Thus, flow rate and the direction of the flow in a two-dimensional plane, i.e., two-dimensional vector of flow can be accurately detected. Moreover, three-dimensional vector of flow can also be detected by employing a two-dimensional transducer array and two-dimensional Fourier transformers.

I claim:

1. An ultrasonic velocity analyzing device comprising:
   a transducer including an array of elements;
   means for driving repeatedly part of said transducer elements in a prescribed interval thereby to repeatedly transmit an ultrasonic wave to a target;
   a parallel reception beam forming means for phase adjusting said signals from said transducer elements and for producing parallel reception signals derived from reception beams with different directivities;
   a sampling means for sampling each of said parallel reception signals and for storing said sampled signals;
   filtering means for performing moving target indication through a differential processing across signals having a certain time duration since transmission;
   a first one-dimension Fourier transform means, including a plurality of outputs, for performing a Fourier transformation with respect to a direction of alignment of the reception beams; and
   a second Fourier transform means including a plurality of outputs for performing a Fourier transformation sequentially for the outputs of said first Fourier transform means with respect to a direction of repetitive transmission,
   wherein lateral velocity and axial velocity of a moving object in said target are obtained from a two-dimensional distribution of the outputs of said second Fourier transform means.

2. An ultrasonic velocity analyzing devices according to claim 1, wherein said parallel reception beam forming means includes means for forming a plurality of reception beams for different angular directions simultaneously.

3. An ultrasonic velocity analyzing device according to claim 1, wherein said parallel reception beam forming means includes means for a plurality of reception beams having a substantially equal focal distance and different angular directions simultaneously.

4. An ultrasonic velocity analyzing device according to claim 1, wherein said parallel reception beam forming means includes a one-dimension Fourier transform means for performing the Fourier transformation for each of the reception signals received by said transducer elements with respect to a direction of alignment of said transducer elements.

5. An ultrasonic velocity analyzing device according to claim 1, further comprising means for obtaining a distribution of velocity vectors on a two-dimensional plane from the outputs of said second Fourier transform means an displaying the distribution on a two-dimension screen.

6. An ultrasonic velocity analyzing device according to claim 1, wherein said filtering means performs the moving target indication for signals from said sampling means or outputs from said first one-dimension Fourier transform means.

7. An ultrasonic velocity analyzing device according to claim 1, wherein said first one-dimension Fourier transform means performs the one-dimensional Fourier transformation for outputs of said sampling means.

8. An ultrasonic flowmeter according to claim 1, wherein said first one-dimensional Fourier transform means performs the one-dimension Fourier transformation for the outputs of said filtering means.

9. An ultrasonic velocity analyzing device comprising:
   a transducer including an array of elements;
   means for driving repeatedly part of said transducer elements in a prescribed interval thereby to repeatedly transmit an ultrasonic wave to a target;
   a parallel reception beam forming means for modifying a phase of signals from said transducer elements and for producing parallel reception signals derived from reception beams with different directivities;
   a sampling means for sampling each of said parallel reception signals and for storing said sampled signals;
   filtering means including a plurality of outputs, for performing moving target indication through a differential processing across signals having a certain time duration since transmission;
   a first one-dimension Fourier transform means, including a plurality of outputs, for performing Fourier transformation with respect to a direction of alignment of the reception beams;

a second Fourier transform means including a plurality of outputs for performing Fourier transformation sequentially for the outputs of said first Fourier transform means with respect to a direction of repetitive transmission, function generation means including a plurality of outputs for generating a prescribed function of space frequency in correspondence to all measurable lateral velocities and axial velocities; and a two-dimensional correlation means for evaluating a two-dimensional correlation function between the outputs of said second Fourier transform means and the outputs of said function generation means, wherein the axial velocity and the lateral velocity are evaluated from the position of a peak value of the output distribution of said two-dimensional correlation means.

10. An ultrasonic velocity analyzing device according to claim 9, wherein said parallel reception beam forming means forms a plurality of reception beams having different angular directions simultaneously.

11. An ultrasonic velocity analyzing device according to claim 9, wherein said parallel reception beam forming means forms a plurality of reception beams having a substantially equal focal distance and different angular directions simultaneously.

12. An ultrasonic velocity analyzing device according to claim 9, wherein said parallel reception beam forming means includes a one-dimensional Fourier transform means for performing Fourier transformation for each of the reception signals received by said transducer elements with respect to a direction of alignment of said transducer elements.

13. An ultrasonic velocity analyzing device according to claim 9, further comprising means for obtaining distribution of velocity vectors on a two-dimensional plane from the outputs of said two-dimension correlation device and displaying the distribution on a two-dimensional screen.

14. An ultrasonic velocity analyzing device according to claim 9, wherein said filtering means performs the moving target indication for signals from said sampling means or outputs from said first one-dimension Fourier transform means.

15. An ultrasonic velocity analyzing device according to claim 9, wherein said one-dimension Fourier transform means performs the one-dimension Fourier transformation for the outputs of said sampling means prior to the filtering operation.

16. An ultrasonic velocity analyzing device according to claim 9, wherein said first one-dimension Fourier transform means performs the one-dimension Fourier transformation for the outputs of said filtering means.

17. An ultrasonic velocity analyzing device comprising:

means for repeatedly transmitting an ultrasonic wave to a target;

a transducer including an array of transducer elements for receiving ultrasonic waves reflected from said target;

a sampling means for sampling signals from said transducer elements;

a Fourier transformer means including a plurality of output for performing Fourier transformation on the signals, which are provided from said transducer elements to be sampled, with respect to a direction of repetitive transmission; and means for deriving a target velocity by analyzing the outputs of said Fourier transformer means on a multi-dimensional plane having a first axis indicating locations of the outputs of said Fourier transformer means and a second axis indicating locations of said transducer elements.

18. An ultrasonic velocity analyzing device comprising:

a transducer including an array of elements;

means for driving repeatedly part of said transducer elements in a prescribed in interval thereby to repeatedly transmit an ultrasonic wave to a target;

a parallel reception beam forming means for phase adjusting signals from said transducer elements and for producing parallel reception signals derived from reception beams with different directivities;

a sampling means for sampling each of said parallel reception signals and for storing said sampled signals;

filtering means for performing moving target indication through a differential processing across signals having a certain time duration since transmission;

a first one-dimension Fourier transform means, including a plurality of outputs, for performing Fourier transformation with respect to a direction of the reception beam alignment; and a second one-dimensional Fourier transform means, including a plurality of outputs, which treats outputs of said first one-dimension Fourier transform means as two-dimension signals of time series corresponding to the transmission of the ultrasonic wave and treats, with respect to a plurality of straight lines coinciding at the origin of a coordinate with respective angles, signals values on each of the straight lines as a one-dimension sequence of numbers to perform the Fourier transformation, wherein lateral velocity and axial velocity of a moving object in said target are obtained from a two-dimensional distribution of the output of said second one-dimension Fourier transform means.

19. An ultrasonic velocity analyzing device according to claim 18, wherein said parallel reception beam forming means forms a plurality of reception beams having different angular directions simultaneously.

20. An ultrasonic velocity analyzing device according to claim 18, wherein said parallel reception beam forming means forms a plurality of reception beams having a substantially equal focal distance and different angular directions simultaneously.

21. An ultrasonic velocity analyzing device according to claim 18, wherein said parallel reception beam forming means includes a one-dimension Fourier transform means for performing Fourier transformation for each of the reception signals received by said transducer elements with respect to a direction of alignment of said transducer elements.

22. An ultrasonic velocity analyzing device according to claim 18, further comprising means for obtaining a distribution of velocity vectors on a two-dimensional Fourier transformer means and displaying the distribution on a two-dimension screen.

23. An ultrasonic velocity analyzing device according to claim 18, wherein said filtering means performs the moving target indication for signals from said sampling means or outputs from said first one-dimension Fourier transform means.

24. An ultrasonic velocity analyzing device according to claim 18, wherein said first one-dimension Fourier transform means performs the one-dimension Fourier transformation for the outputs of said sampling means prior to the filtering means.

25. An ultrasonic velocity analyzing device according to claim 18, wherein said first one-dimension Fourier transform means performs the one-dimension Fourier transformation for the outputs of said filtering means.

26. An ultrasonic velocity analyzing device comprising:
   a transducer including an array of elements;
   means for driving repeatedly part of said transducer elements in a prescribed interval thereby to repeatedly transmit an ultrasonic wave to a target;
   a parallel reception beam forming means for modifying phrases of signals from said transducer elements and for producing parallel reception signals derived from reception beams with different directivities;
   a sampling means for sampling each of said parallel reception signals and for storing said sampled signals;
   filtering means including a plurality of outputs, for performing moving target indication through a differential processing across signals having a certain time duration since transmission;
   a first one-dimension Fourier transform means, including a plurality of outputs, for performing Fourier transformation with respect to a direction of alignment of the reception beams;
   a second one-dimension Fourier transform means, including a plurality of outputs, which treats the outputs of said first one-dimension Fourier transform means as two-dimension signals of time series corresponding to the transmission of the ultrasonic wave and treats, with respect to a plurality of straight lines coinciding at the origin of a coordinate with respective angles, signal values on each of the straight lines as a one-dimensional sequence of numbers to perform the Fourier transformation; and
   a coordinate transform means, including a plurality of outputs, which transforms the outputs of said second one-dimension Fourier transform means to a lateral velocity and an axial velocity of a moving object,
   wherein the lateral velocity and the axial velocity of a moving object in said target are obtained.

27. An ultrasonic velocity analyzing device according to claim 26, wherein said parallel reception beam forming means forms a plurality of reception beams having different angular directions simultaneously.

28. An ultrasonic velocity analyzing device according to claim 26, wherein said parallel reception beam forming means forms a plurality of reception beams having a substantially equal focal distance and different angular directions simultaneously.

29. An ultrasonic velocity analyzing device according to claim 26, wherein said parallel reception beam forming means including a one-dimensional Fourier transform means for performing Fourier transformation for each of the reception signals received by said transducer elements with respect to a direction of alignment of said transducer elements.

30. An ultrasonic velocity analyzing device according to claim 26, further comprising means for obtaining a distribution of velocity vectors on a two-dimensional plane from the outputs of said coordinate transform means and displaying the distribution on a two-dimensional screen.

31. An ultrasonic velocity analyzing device according to claim 26, wherein said filtering means performs the moving target indication for signals from said sampling means or outputs from said first one-dimension Fourier transform means.

32. An ultrasonic velocity analyzing device according to claim 26, wherein said first one-dimension Fourier transform means performs the one-dimension Fourier transformation for outputs of said sampling means prior to the filtering means.

33. An ultrasonic velocity analyzing device according to claim 26, wherein said first one-dimension Fourier transform means performs the one-dimension Fourier transformation for the outputs of said filtering means.

34. An ultrasonic velocity analyzing device comprising:
   means for repetitive transmission of ultrasonic waves;
   a receiving array transducer elements for receiving reflection signals of said ultrasonic waves;
   means for converting received signals into phase delay and amplitude information;
   means for converting the received signals with the phase delay and amplitude information into a multi-dimensional function with parameters related to a spatial location and time of each transmission; and
   means for converting the multi-dimensional function into a multi-dimensional velocity vector.

35. An ultrasonic velocity analyzing device comprising:
   a transducer including an array of elements;
   means for driving repeatedly part of said transducer elements in a prescribed interval thereby to repeatedly transmit an ultrasonic wave to a target;
   a first one-dimension Fourier transform means, including a plurality of outputs, for performing Fourier transformation with respect to a direction of alignment for signals from said transducer elements; and
   a second one-dimension Fourier transform means which treats the outputs of said first one-dimension Fourier transform means as two-dimension signals of time series corresponding to the transmission of the ultrasonic wave and treats, with respect to a plurality of straight lines coinciding at an origin of a coordinate with respective angles, signal values on each of the straight lines as a one-dimension sequence of numbers to perform the Fourier transformation;
   wherein the lateral velocity and the axial velocity of a moving object in said target are obtained.

36. An ultrasonic velocity analyzing device comprising:
   means for repeatedly transmitting an ultrasonic wave to a target;
   a transducer including an array of transducer elements for receiving ultrasonic waves reflected from said target;
   a sampling means for sampling signals from said transducer elements;
   a Fourier transducer means, including a plurality of outputs, for performing Fourier transformation on the signals, which are provided from said transducer elements to be sampled, with respect to a direction of said transducer elements; and means for deriving a target velocity by analyzing the outputs of said Fourier transformer means on a multi-dimensional plane having a first axis indicating locations of the outputs of said Fourier transformer means and a second axis indicating a direction of repetitive transmission.

* * * * *